United States Patent [19]

Tisdale et al.

[11] Patent Number: 5,219,579
[45] Date of Patent: Jun. 15, 1993

[54] BIOLOGICALLY ACTIVE MATERIAL CHARACTERIZED BY CATABOLIC ACTIVITY GENERALLY ASSOCIATED WITH CACHEXIA-INDUCING TUMORS, PREPARATIONS, PRODUCTION AND USES THEREOF

[75] Inventors: Michael J. Tisdale, Claverdon; Susan A. Beck, Willenhall, both of United Kingdom

[73] Assignee: Cancer Research Campaign Technology Limited, London, United Kingdom

[21] Appl. No.: 372,340
[22] PCT Filed: Mar. 20, 1989
[86] PCT No.: PCT/GB89/00296
§ 371 Date: Jun. 2, 1989
§ 102(e) Date: Jun. 2, 1989
[87] PCT Pub. No.: WO89/08709
PCT Pub. Date: Sep. 21, 1989

[30] Foreign Application Priority Data

Mar. 18, 1988 [GB] United Kingdom ................ 8806471

[51] Int. Cl.$^5$ .............................................. A61K 35/12
[52] U.S. Cl. ..................................... 424/573; 530/300
[58] Field of Search ......................... 424/573; 530/300

[56] References Cited

FOREIGN PATENT DOCUMENTS 0212489 3/1989 European Pat. Off. .

OTHER PUBLICATIONS

Kitada et al. CA 96:178891 (1982).
Kitada et al. CA 99:20427 (1983).
UK Search Report re 8906371.
International Search Report re PCT/GB 89/00296.
European Search Report EP 89 30 2740.
Beck, Susana.; Tisdale, Michael J., "Production of lipolytic and factors by a murine tumor-producing cachexia in the host" CHEMLABS Journal 08(05)035641, Pharm. Sci. Inst. Aston Univ. Birmingham UK GB B4 7ET Cancer Res.: (87) P 5919-23; vol. 47; No. 22.
Tisdale, J. J.; Beck, S. A., "Cachetic Factors Produced by Human and Animal Tumors" Proceedings of AACR vol. 29, Mar. 1988 p. 60, 79th Annual Meeting of the American Association for Cancer Research, New Orleans, May 25-28.
14 Mammalian Pathol. Biochem. vol. 106, 1987 #4 Jul. 27, 1987.
Kekwick and Pawan, "Fat Mobilizing Substance (FMS)", Medical Unit and Institute of Clinical Research, the Medical School, London, England, Nov. 21, 1966 in Metabolism, 16, 787-796 (1967).
Kitada et al Lipolysis Induction in Adipocytes by a Protein from Tumor Cells, J. Cell. Biochem., 2(4), 1982, pp. 409-416.
Kitada et al, Characterization of a Lipid Mobilizing Factor from Tumors, Prog. Lipid Res., 20(1-4), 1981, pp. 823-826.

*Primary Examiner*—Douglas W. Robinson
*Assistant Examiner*—Jean C. Witz
*Attorney, Agent, or Firm*—Cushman, Darby & Cushman

[57] ABSTRACT

A biologically active lipolytic factor having an average molecular weight substantially less than 5000 daltons and comprising active molecular species having molecular weights of about 3000 daltons, 1500 daltons and 700-800 daltons is disclosed. The factor can be isolated, using chromatographic methods, from cachexia-inducing tumours, cultures of tissue cells of cachexia-inducing tumours especially cultures of a MAC16 tumour cell line, or from body fluids such as serum or urine of mammals bearing cachexia-inducing tumours. Cancer diagnostic applications in relation to human individuals are described as well as uses for screening and identifying potential anti-cachetic and/or antitumour therapeutic agents.

9 Claims, 18 Drawing Sheets

A. MAC16 cell line
B. Media from MAC16 cell line
C. MAC16 tumour in vivo

BIOLOGICALLY ACTIVE MATERIAL CHARACTERIZED BY CATABOLIC ACTIVITY GENERALLY ASSOCIATED WITH CACHEXIA-INDUCING TUMORS, PREPARATIONS, PRODUCTION AND USES THEREOF

The present invention relates to the field of biochemistry and medicine, especially in connection with biologically active material characterised by catabolic activity, particularly lipolytic activity, generally associated with cachexia-inducing tumours.

BACKGROUND

For convenience, publications relating to the following description of the background of the invention are numerically referenced and listed in the appended bibliography.

Evidence (see references 1 to 7) has previously been reported indicating that at least some malignant tumours in mammals, especially cachexia-inducing tumours, give rise to the production of one or more catabolic factors which may be found in the circulatory system, e.g. in blood plasma.

It is well known that cachexia, characterised by progressive weakness, dramatic weight loss and wasting, is a common condition arising in many human cancer patients, especially in patients with gastrointestinal or lung cancer, and this often appears to be the most frequent cause of eventual death in such patients. Since, however, cachexia at least in human patients generally arises, often at an early stage, when the tumour mass is only a very small proportion of body weight it cannot be generally explained by a simple competitive effect between the tumour and body tissues for available nutrients; also, although in some cases cancer cachexia is accompanied by anorexia manifested by a severely reduced food and water intake, anorexia does not occur in all cases or appears only after severe loss of weight and body tissues (fat and muscle) has already become established; anorexia cannot therefore be recognised as a primary cause of all or many cancer cachectic conditions, and it seems possible that catabolic factors arising from the tumour and acting more directly on the host tissues may be primarily responsible.

Additionally, there is also some evidence indicating that growing tumours may derive at least part of the fatty acids they require, e.g. for membrane formation, from tissues of their host, and that in at least some cases these fatty acids may be derived from the fats in adipose tissue of the host through the action of a lipolytic catabolic factor that may be found in the host's circulatory system in the presence of the tumour. However, although this may be deemed suggestive of a possible link or causal relationship between such lipolytic factor, other catabolic factors possibly present, the growing tumour, and symptoms of cachexia independent of anorexia, various previous attempts (references 3, 4, 5, 6 and 7) to isolate, identify and characterise a lipolytic factor of this kind have produced somewhat confusing, uncertain, and inconsistent results and there has also been substantial doubt as to the extent of dependence of any such lipolytic factor on tumour specificity.

Thus, in 1980 it was reported by Kitada et al (reference 3) that the serum of AKR mice bearing thymic lymphoma contained a potent lipid mobilizing factor having lipolytic activity as evidenced by comparative in vivo assaying of the breakdown of adipose tissue labelled with radioactive carbon implanted into test animals of which some were injected with samples of the serum, measurements being taken of the radioactive carbon appearing in the respiratory $CO_2$. The same effects of breakdown of the implanted adipose tissue were also observed upon injecting samples of extracts of the tumours and also upon injecting samples of culture medium from an AKR mouse lymphoma cell culture. These results were also reported again in 1981 (reference 4) by the same investigators, together with the additional result of a similar adipose tissue breakdown effect being observed upon in vivo assaying in the same way a serum sample from a human cancer patient with adenocarcinoma. In addition, the results then reported (somewhat superfically) also included the results of a preliminary attempt to isolate and characterise the active substance by a gel filtration technique involving chromatographing a dilute acetic acid extract of the thymic lymphoma tumour tissue using a Bio-Gel P6 column from which the various fractions were again tested for lipolytic activity by the same in vivo assay technique. It was then deduced from these results that the active lipolytic factor was a small "heat stable" protein having a molecular weight of about 5000 daltons. However, this conclusion was not substantiated by later results (see below) and, in any event, it will be appreciated that use of the in vivo assaying technique did not necessarily exclude the possibility that the test samples injected merely triggered the production of, or activated, a lipolytic factor within the test animal instead of the test samples themselves containing the active lipolytic factor.

Subsequently, Kitada et al reported in 1982 (reference 5) that after continuing their investigations using extracts of thymic lymphoma tumour tissue from AKR mice, using an in vitro technique for assaying lipolytic activity involving the measurement of liberated glycerol after incubation of samples of the tumour tissue extracts with preparations of rat adipocytes, lipolytic activity could only be detected after ageing of the extracts kept at low temperature (4° C.) for several days. Following chromatographic gel filtration of such aged active extracts, whose activity was found to be completely destroyed by digesting with trypsin, they then concluded that the lipolytic active substance which they had detected was formed by aggregation of inactive small protein molecules.

The presence of a lipolytic factor in ascites fluid from DDK mice with sarcoma 180 and in ascites fluid from human cancer patients with hepatoma has also been reported by Masuno et al (references 6 and 7) but in this case their experimental evidence indicated that the lipolytic factor found, termed Toxohormone-L, was an acidic protein of high molecular weight (of the order of 65,000 to 75,000 daltons) which acted indirectly by suppressing food and water intake, thereby promoting anorexia as the main cause of breakdown of adipose tissue and symptoms of cachexia.

Similarly, a macrophage product tumour necrosis factor (TNF) and the homologous or related substance cachectin (see references 10 and 11) which inter alia inhibit lipoprotein lipase activity and induce weight loss have also been implicated as agents concerned in causing cancer cachexia, but again any cachectic effects arising from this source appear to be caused primarily by anorexic effects or dehydration (see reference 12).

It is necessary to recognise, however, that the conditions in experimental animals such as mice and rats bearing tumours of the kind mentioned above may not properly reflect the conditions present in human cancer patients afflicted with cachexia-inducing tumours, especially bearing in mind that in rodents many such tumours grow relatively rapidly and that evidence of cachexia is often apparent, if at all, only at a stage when the tumour has reached a size equivalent to 30-40% of total body weight. In contrast, in humans tumour growth is slower and tumour mass rarely reaches or exceeds 5% of total body weight although symptoms of cachexia often arise whilst the tumour mass is but a small fraction of 1% of total body weight. Nevertheless, there has been a promising development for improving the conditions for experimental investigations following studies more recently reported (references 1 and 2) on mice (pure NMRI strain) bearing a tumour designated MAC16, first described by Cowen et al (see reference 8), of an established series (MAC) of chemically induced, transplantable colon adenocarcinomas, this MAC16 tumour being produced by a particular cell line now deposited on Mar. 8, 1989 in the European Collection of Animal Cell Cultures (ECACC) at the Public Health Laboratory Service Centre for Applied Microbiology and Research, Porton Down, Salisbury, Wiltshire, United Kingdom under a provisional accession number 8903016.

The MAC16 tumour is a moderately well-differentiated adenocarcinoma which has been serially passaged in mice for many years, and it has been found that it appears to represent a more satisfactory experimental model for tumours which induce cachexia in human patients, especially insofar as it has often been found to produce substantial loss of body weight at small tumour burdens (less than 1% body weight) and without a reduction in the intake of either food or water (reference 1).

Some of these recently reported studies (reference 2) have further indicated that the MAC16 tumour in mice gives rise to the production of circulatory catabolic factors, apparently comprising both a lipolytic factor and a proteolytic factor, which seem to be present in the plasma of the tumour-bearing animals and which, it could be postulated, might be directly responsible at least to some extent for the breakdown of the body fat and muscle tissues, and hence for symptoms of cachexia. More particularly, the lipolytic factor was reported as having a lipolytic activity (as measured either in tumour extracts or plasma samples incubated with mouse epididymal adipose tissue followed by use of an in vitro free fatty acid assaying technique) which is non-dialysable, which is destroyed by heat and acid, and which is inhibited by insulin and 3-hydroxybutyrate. However, no more precise characterisation or isolation of this factor was reported, although in a later paper (reference 12) evidence has been presented showing that it is not the same as, and is clearly distinguished from, cachectin or tumour necrosis factor (TNF) referred to earlier.

SUMMARY OF THE INVENTION

The present invention has arisen out of further studies investigating the above-mentioned catabolic factors associated with at least MAC16 adenocarcinoma tumours in mice. More particularly, the invention is especially but not exclusively concerned with the material constituting the lipolytic factor referred to, its isolation, its more complete identification, purification and characterisation, and applications thereof including diagnostic methods or materials and pharmaceutical or therapeutic compositions derived therefrom or associated with said lipolytic factor.

During these further studies it was found initially that these catabolic factors, or at least the lipolytic factor concerned, may be isolated and separated into active functional components by fractionating freshly prepared extracts of a MAC16 tumour and/or samples of body fluids from tumour bearing animals using separation and/or concentration techniques involving ion-exchange column chromatography employing a cationic stationary phase such as DEAE (diethylaminoethyl) cellulose and eluting over a range of ionic strengths under a salt gradient. Lipolytically active fractions thus obtained could then be further resolved by gel filtration or exclusion chromatography, e.g. using a modified Dextran gel such as a Sephadex (Trade Mark) gel of appropriate porosity grade, to yield purified or at least partially purified preparations of at least the active lipolytic factor, or active components thereof, in fractions corresponding to elution volumes representative of molecular weights substantially less than 5000 daltons, and generally less than 4000 daltons, approximating for instance to 3000 daltons, 1500 daltons and 750 (within range 700 to 800) daltons.

The effectiveness of the DEAE cellulose ion exchange chromatography using a salt gradient demonstrates that the active lipolytic substance, at least in solution, is characterised by having a negative charge. For isolating and identifying the substance, however, it has also been found that the above-mentioned first stage of ion-exchange chromatography can be omitted and that samples containing the active lipolytic factor can be subjected directly to gel filtration or exclusion chromatography in the manner described, again to yield active preparations of the factor having the same approximate molecular weights or distribution pattern of molecular weights.

The lipolytic activity of the preparations from the Sephadex exclusion chromatography, as evidenced by in vitro assaying of glycerol released upon incubation with mouse adipose tissue cell preparations, has been found to reflect the lipolytic activity found in the source material, e.g. tumour extracts or serum samples from the tumour bearing animals, possibly at an enhanced level consequent to the isolation and purification procedure, and this activity has now been found to be relatively stable to heat (e.g. substantially unaffected by the preparations being maintained at 90° C. for 15 minutes), acid stable (well below pH 1) and stable to trypsin and chymotrypsin as well as being unaffected by RNAase or DNAase.

The above characteristics, including the molecular weight range and the fact that no ageing has been found to be necessary for the development of lipolytic activity, sharply contrast with the characteristics of the lipid mobilising factors reported by Kitada et al in the references previously mentioned (references 3, 4, 5), and are unlike those of any other known lipolytic or cachetic factors. Moreover, the activity is also resistant to periodate so that the substance is clearly not an oligosaccharide, and whilst the activity may be destroyed or reduced by alkaline phosphatase it is not thought likely that the substance is a phospholipid. On the other hand the activity has been found to be at least partially destroyed by pronase and, although it appears to be unaffected by trypsin and chymotrypsin, this characteristic, and the molecular weight characteristics at least, together indicate that the activity resides in polypeptide or low molecular weight protein material which is hormone like, not being a lipase, but unlike any common hormone in this size range. Also, the active substance has now been found to be dialysable in solution under normal conditions. In addition, it has been confirmed that the lipolytic activity is inhibited by insulin and by 3-hydroxybutyrate.

Furthermore, isoelectric focussing experiments on preparations of this active lipolytic factor have shown that it has a very low isoelectric point, at a pH of less than 1.

Instead of tumour extracts being used as a biological source material for providing the lipolytic factor, preparations derived from tumour cell cultures may be used as an alternative, often preferable, source. Suitable body fluid sources include blood plasma and serum, or urine, in many cases urine being the preferred source material, especially for diagnostic purposes as hereinafter described.

It has moreover been found that the same lipolytic factor appears also to be associated, albeit often at a lower level, with tumours that do not produce symptoms of cachexia, and furthermore it appears to be present in body fluids, especially serum or urine, of at least most human cancer patients, even cancer patients without symptoms of cachexia. Again, however, it is usually most evident in body fluids of cancer patients afflicted with cancer cachexia and samples of urine or serum from such patients, when compared with controls, again show an elevated lipolytic activity apparently related at least qualitatively to the degree of weight loss as with mice bearing the MAC16 tumour (see later—Table 1). Upon subjecting such human body fluid samples to the same DEAE cellulose ion exchange chromatography procedure as used for the MAC16 tumour extracts it has been found that elution of lipolytically active fractions occurs at substantially the same ionic strength as with the lipolytic factor from extracts of the MAC16 tumour. In contrast, samples of serum from control subjects when subjected to the same procedure provide no fractions having a corresponding significant lipolytic activity. Furthermore, when these active fractions from the DEAE cellulose chromatographic separation, or the original body fluid samples (preferably urine samples) of the cancer patients, are subjected to Sephadex gel filtration, they have been found to be resolvable into active components having molecular weight characteristics corresponding at least substantially to those obtained from similar chromatographic separation procedures carried out on the extracts prepared from the MAC16 tumours, including in particular components having respective molecular weights of about 750 daltons and 1500 daltons and usually another component about or slightly greater than 3000 daltons but less than 4000 daltons.

This finding provides the basis, in accordance with one aspect of the invention, of a practical method of diagnosis for detecting the presence of a tumour in a human patient, or indeed in other mammals, or for monitoring the progress of treatment of a tumour, e.g. after administering antitumour drugs, such method involving taking a sample of body fluids such as urine or blood serum and testing for the presence of the lipolytic factor or material herein disclosed and characterised. This testing may be carried out by ion-exchange and/or gel filtration chromatographic separation techniques seeking to isolate and identify the lipolytic material, e.g. by determining the characteristic elution ionic strengths of fractions from a DEAE cellulose column and/or by identifying the characteristic distribution pattern of the molecular weight of active components when fractionated through an appropriate Sephadex gel filtration column, or the like, the fractions being assayed for lipolytic activity substantially as herein described. Alternatively, any other suitable method of separation and/or assaying or testing may be used. In this connection, preparations of the active lipolytic material in purified or partially purified form, prepared for example from MAC16 tumour tissue as herein described, may usefully be utilised to provide comparative standards for diagnostic purposes.

Preparations of the purified active lipolytic material are especially useful for providing antigenic material enabling antibodies to be raised as hereinafter set forth, such antibodies and uses thereof forming a further important aspect of the invention.

Antibodies, especially monoclonal antibodies, capable of specifically recognizing and binding to the active lipolytic factor can provide a valuable biochemical reagent for detecting and measuring the amount of this factor; indeed, in practice, it is envisaged that monoclonal antibodies will often provide the most convenient and preferred diagnostic agent for use in detecting and measuring the active lipolytic factor, employing any suitable assaying technique known in the art including, for example, conventional radioimmunoassay (RIA) or so-called immunoradiometric (IRMA) methods.

In addition, however, since such antibodies or monoclonal antibodies can generally be expected to act as antagonists which will block and destroy or inhibit the activity of the lipolytic factor, and since the latter is believed generally to play a vital role and to be involved in many cases of cancer cachexia and/or tumour growth as hereinafter described, antibodies can also have an important therapeutic value as agents for treating and suppressing the symptoms of cachexia and/or possibly for inhibiting or reducing tumour growth. In respect of the latter possibility, it should be noted that even tumours which do not generally induce cachexia now appear also to produce at least low levels of the same lipolytic factor.

Such antibodies or monoclonal antibodies, especially if specific for particular molecular weight species of the lipolytic factor such as the 1500 daltons species or, preferably, the 700–800 daltons species, can also be valuable for use in preparing further purified quantities of the substance. For this purpose they may, for example, be immobilized on a suitable solid support which is then employed in known manner in an affinity purification procedure applied to impure or less pure preparations of material containing the lipolytic factor.

In accordance with another aspect of the invention the purified or at least partially purifed preparations of this lipolytic factor or material are also useful for screening and in promoting investigation of possible activity inhibiting agents to identify substances or compounds having potential as therapeutic or antitumour agents, e.g. for treating cachectic conditions and controlling growth of solid tumours.

Preparations of the lipolytic material herein disclosed are also at least potentially useful for the controlled treatment of obesity in mammals, including humans, for medical or cosmetic purposes. For this application therapeutically useful quantities of the essentially pure active material may be made up or combined in admixture with any suitable pharmaceutically acceptable carrier in accordance with known methods to provide a pharmaceutically useful composition or formulation.

Although at present the isolation and separation procedures which are herein specifically described are preferred procedures for purification of the active lipolytic material, other methods of purification may also be used as alternatives, including for example reverse phase high performance liquid chromatography, differential salt precipitation, SDS polyacrylamide gel electrophoresis, isoelectric focusing, paper electrophoresis, and the like, and these are also all deemed to fall within the scope of the invention.

Accordingly, from one aspect, the invention provides a novel biologically active lipolytic material composed essentially of a purified or partially purified lipolytically active constituent characterised in that it:
  a) has an average molecular weight substantially less than 5000 daltons and comprises at least one active molecular species of which the molecular weight is about 1500 daltons or less;
  b) is obtainable from at least cachexia-inducing tumours and/or from cultures of tissue cells of cachexia-inducing tumours and/or from body fluids such as urine or blood serum of mammals bearing cachexia-inducing tumours by subjecting extracts of said tumours or of tissue cell cultures or samples of said body fluids to an isolation/purification procedure that includes at least one stage of exclusion chromatography employing a filtration gel effective under the conditions of use for retaining at least material having a molecular weight in the range of 600 to 4000 daltons.

The active lipolytic material or the lipolytically active constituent thereof in accordance with the invention may be further characterised by the fact that it is heat stable.

The active lipolytic material or the lipolytically active constituent thereof in accordance with the invention may be further characterised by the fact that it is acid stable.

The active lipolytic material or the lipolytically active constituent thereof in accordance with the invention may be further characterised by the fact that it is dialysable.

The active lipolytic material or the lipolytically active constituent thereof in accordance with the invention may be further characterised by the fact that it is negatively charged and acidic in solution.

The active lipolytic material or the lipolytically active constituent thereof in accordance with the invention may be further characterised by the fact that it has an isoelectric point as determined by isoelectric focussing at a pH of less than 1.

The active lipolytic material or the lipolytically active constituent thereof in accordance with the invention may be further characterised by the fact that it comprises an acidic polypeptide.

The active lipolytic material or the lipolytically active constituent thereof in accordance with the invention may be further characterised by the fact that insofar as its lipolytic activity is concerned it is resistant to trypsin, chymotrypsin, periodate, RNAase and DNAase, but it is partially destroyed or inactivated by pronase and alkaline phosphatase.

The active lipolytic material or the lipolytically active constituent thereof in accordance with the invention may be further characterised by the fact that it produces weight loss cachectic symptoms when administered by injection to healthy non-tumour bearing mice.

The active lipolytic material or the lipolytically active constituent thereof in accordance with the invention may be further characterised by the fact that when incubated in vitro with at least adipocytes prepared from mouse adipose tissue, it is effective in raising the level of cyclic adenylic acid (cAMP) in such cells over an extended period.

The active lipolytic material or the lipolytically active constituent thereof in accordance with the invention may be further characterised by the fact that it is obtainable using an isolation/purification procedure which includes a preliminary stage of ion-exchange column chromatography employing a cationic stationary phase, e.g. DEAE cellulose, and elution over a range of ionic strengths under a salt gradient.

The active lipolytic material or the lipolytically active constituent thereof in accordance with the invention may be further characterised by the fact that it comprises an active molecular species of which the molecular weight is in the range of about 700-800 daltons.

The active lipolytic material or the lipolytically active constituent thereof in accordance with the invention may be further characterised by the fact that it comprises another active molecular species of which the molecular weight is about 3000 daltons.

The active lipolytic material or the lipolytically active constituent thereof in accordance with the invention may be further characterised by the fact that it comprises three active molecular species of which the molecular weights are approximately in the ratio of 1:2:4.

The active lipolytic material or the lipolytically active constituent thereof in accordance with the invention may be further characterised by the fact that it comprises a plurality of active molecular species which are in chemical equilibrium.

The active lipolytic material or the lipolytically active constituent thereof in accordance with the invention may be further characterised by the fact that it comprises a plurality of active molecular species formed by a lower molecular weight species aggregating to produce higher molecular weight species in the presence of metal ions, said higher molecular weight species being susceptible to breakdown into the lower molecular weight species by metal chelating agents such as EDTA.

The active lipolytic material or the lipolytically active constituent thereof in accordance with the invention may be further characterised by the fact that it is resolvable by exclusion chromatography using a Sephadex G50 column or equivalent to provide a lipolytic activity distribution pattern of eluted fractions having main activity peaks corresponding to a molecular species having a molecular weight of about 1500 daltons and to a molecular species of which the molecular weight is in the range of about 700-800 daltons and/or a molecular species which the molecular weight is about 3000 daltons.

The active lipolytic material or the lipolytically active constituent thereof in accordance with the invention may be further characterised by the fact that its lipolytic activity, at least when incubated with adipocytes from mouse adipose tissue, is inhibited by compounds selected from the group comprising hypoxanthine, Salbutamol, tolbutamide and 5,8,11,14,17-eicosapentaenoic acid or a triglyceride ester thereof.

Alternatively, novel biologically active lipolytic material provided by the invention may be defined as material obtained as herein specified which is purified to such an extent as to return only a molecular weight value or values of less than 4000 daltons for the major activity peak or peaks when subjected to gel filtration exclusion chromatography.

The invention also provides methods of preparing the aforesaid purified or partially purified biologically active lipolytic material, or lipolytically active constituent thereof, as herein set forth.

Some or all of the active components of different molecular weights into which the naturally derived lipolytic material is resolvable, as referred to above, may comprise a common functional molecular grouping directly related to or responsible for said lipolytic activity, and the invention further extends to biologically active lipolytic compounds or substances, including homologues and derivatives, containing said common functional molecular grouping.

The invention also provides diagnostic methods for detecting the presence of a tumour in mammals, especially but not exclusively a cachexia-inducing tumour, and/or for monitoring the progress of therapeutic treatment of such tumours, said methods comprising taking a sample of body fluid such as urine or blood serum and testing to detect the presence of and/or to measure the aforesaid active lipolytic material or substance. Self-contained diagnostic kits may be provided for this purpose.

The invention also provides a method for in vitro screening of various substances or compounds to identify those which are possible antagonists to or inhibitors of the lipolytic factor herein disclosed and which thereby may have potential as anti-cachectic or antitumour therapeutic agents. The invention also relates to antilipolytic agents initially identified by such screening methods and used for the manufacture of medical preparations or medicaments for the treatment of cancer-associated cachexia and/or tumours.

The invention further provides preparations of the aforesaid active lipolytic material for therapeutic purposes, and pharmaceutical formulations thereof, useful for example in the treatment or control of obesity, and it also provides material for use in raising antibodies which may then be produced in quantity, e.g. by use of known hybridoma production and cloning techniques to produce monoclonal antibodies useful as diagnostic agents and/or as therapeutic agents.

Thus, the invention further embraces antibodies to the lipolytic factor, or to particular active molecular components thereof, and methods for their production.

Antibodies according to the invention may be, for example, whole antibodies or fragments thereof. Particular antibody fragments include those obtained by proteolytic cleavage of whole antibodies, such as F(ab')$_2$, Fab' or Fab fragments; or fragments obtained by recombinant DNA techniques, for example Fv fragments (as described in International Patent Application No. PCT/GB 88/00747).

The antibody or antibody fragment may in general belong to any immunoglobulin class. Thus, for example, it may be an immunoglobulin M (IgM) antibody or, in particular, an immunoglobulin G IgG) antibody. The antibody or fragment may be of animal, for example mammalian, origin and may be for example of murine, rat or human origin. It may be a natural antibody or a fragment thereof, or, if desired, a recombinant antibody or antibody fragment, i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted in to the variable framework regions of a second, different antibody (as described in European Patent Specification No. 239400); (2) recombinant antibodies or fragments wherein non-Fv sequences have been substituted by non-Fv sequences from other, different antibodies (as described in European Patent Specifications Nos. 171496, 172494 and 194276); or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Specifications Nos. WO 89/01974 and WO 89/01782 respectively).

The antibody or antibody fragment may be of polyclonal, or, preferably, monoclonal origin. It may be polyspecific, but is preferably monospecific for the lipolytic material of the invention.

Whole antibodies according to the invention may be prepared using well-known immunological techniques employing the purified active lipolytic material from any source as antigen. Thus, for example, any suitable host may be injected with the lipolytic material and the serum collected to yield the desired polyclonal antibody after appropriate purification and/or concentration (for example, by affinity chromatography using immobilised lipolytic material as the affinity medium). Alternatively, splenocytes or lymphocytes may be recovered from the injected host and immortalised using for example the method of Kohler et al., *Eur. J. Immunol* 6, 511, (1976), the resulting cells being segregated to obtain a single genetic line producing monoclonal antibodies in accordance with conventional practice.

It will be appreciated that in the above methods the lipolytic material may be of a size that does not elicit a suitable immune response in the host, even though it may be antigenic and capable of binding to specific antibodies. It may, therefore, be preferable covalently to link the material to a large carrier molecule which is itself immunogenic, and to use the resulting conjugate compound as the antigen, again in accordance with conventional practice [see for example, D. M. Weir, in *"Handbook of Experimental Immunology"* 3, 2nd ed. pp A2.10 –A2.11. Blackwell Scientific Publications, Oxford, 1973; and M.Z.Atassi and A.F.S.A. Habeeb, in *"Immunochemistry of Proteins"* (M.Z.Atassi, ed), 2, pp 177–264, Plenum, New York, 1977].

Antibody fragments may be produced using conventional techniques, for example by enzymatic digestion, e.g. with pepsin [Lanoyi and Nisonoff, *J. Immunol. Meth.*, 56, 235, (1983)]. Where it is desired to produce recombinant antibodies according to the invention these may be produced using for example the general methods described in the above mentioned patent specifications.

The invention also includes all novel and inventive features and aspects herein disclosed, either explicitly or implicitly and either singly or in combination with one another, and the scope of the invention is not to be construed as being limited by the illustrative examples or by the terms and expressions used herein merely in a descriptive or explanatory sense.

MORE DETAILED DESCRIPTION

Examples hereinafter presented illustrate at least some aspects of the invention in more detail, but there first follows an outline or summary of the materials, methods and techniques which have generally been used in the illustrative examples unless subsequently stated otherwise.

Animals

Pure strain Balb/c and NMRI mice were purchased from Banting and Kingman, Hull (U.K.). They were fed on a rat and mouse breeding diet (Pilsbury, Birmingham, U.K.) and water ad lib.

Preparation of Tumour Homogenate Extracts and Tumour Tissue Culture Extracts Fragments of the MAC16 tumour (obtained initially from Dr. J. A. Double, University of Bradford, U.K.) excised from donor animals (as described in references 1 and 2) were implanted in the flank of NMRI mice by means of a trocar. Usually tumours were removed 14 to 42 days after transplantation and were homogenised at 4° C. in Krebs-Ringer bicarbonate buffer pH 7.6 and centrifuged, e.g. for ten minutes at 3,000 rpm to remove debris. In some cases, the supernatants obtained in this way from several MAC16 tumours were combined together to provide a greater quantity of extract material.

In a typical procedure for preparing tumour tissue culture extracts from MAC16 cell cultures grown in a medium comprising, for example, RPM1/1640 nutrient plus HEPES and with or without foetal calf serum (10%), 500 ml of the culture medium obtained by centrifuging MAC16 cell suspensions at 3000 rpm for 5 minutes was lyophilized overnight and the solid residue was reconstituted with 10 ml water with warming to aid solubility. The extract was then transferred to a clean tube and centrifuged at 5000 rpm for 15 min. The supernatant was used as a crude preparation of the lipolytic factor.

DEAE Cellulose Column Chromatography

In using this technique, freshly prepared crude tumour homogenate or tissue culture extract supernatants were fractionated by anion exchange chromatography using a DEAE cellulose column and eluting under a salt gradient. The DEAE cellulose column (usual dimensions 1.6×30 cm) was equilibrated with 0.01M phosphate buffer, pH 8.0. Material was eluted from the column using a linear gradient of 0 to 0.2M NaCl in 0.01M phosphate buffer, pH 8.0. The column was run at a flow rate of 30.0 ml/hr and the effluent from the column was collected in 5 ml fractions. Tumour extract samples applied to the column generally contained 1.3 mg of tumour protein. The lipolytic activity of each fraction was measured by a lipolytic assay technique carried out as detailed below.

Lipolytic Assay

Balb/c and MF1 mice were killed by cervical dislocation and their epididymal adipose tissue was quickly removed and minced in Krebs-Ringer bicarbonate buffer, pH 7.6. The adipose tissue was incubated at 37° C. in Krebs-Ringer bicarbonate buffer containing collagenase 1.5-2.0 mg/ml). The cells were gassed prior to incubation with a gaseous mixture of 95% $O_2$:5% $CO_2$. After 2 hr the cells were washed with the Krebs-Ringer buffer 5 times to eliminate any traces of collagenase still present. The cells were then counted using a haemocytometer and suspended in the appropriate amount of the Krebs-Ringer buffer to give $1-2\times10^5$ adipocytes per ml. 1 ml of cells were then gassed again with 95% $O_2$:5% $CO_2$ and incubated with the appropriate test substance for 2 hr at 37° C. The concentration of glycerol in the incubations was determined enzymatically by the method of Wieland (see reference 9). Control samples containing adipocytes alone were also analysed to measure any spontaneous glycerol release. When assaying serum samples a control of serum alone (no adipocytes) was also assayed to measure the initial amount of glycerol present in the serum.

Glycerol determination

To 0.5 ml of incubation buffer was added 0.5 ml of perchloric acid (10% w/v) and the mixture was shaken to ensure total deproteinisation. The precipitated protein was sedimented by centrifugation at 2,000 rpm for 10 min and the supernatant was aspirated using a Pasteur pipette. The supernatant was then neutralised with KOH (20% w/v) after which the volume was noted (this gives the dilution factor used in subsequent calculations). The potassium perchlorate precipitate was sedimented by centrifugation (2,000 rpm for 10 min) and the supernatant was aspirated. Assays were then either performed immediately or after storage at −20° C. for approximately 18-72 hours. Glycerol was determined enzymatically by the coupled enzyme systems:

GLYCEROL $\xrightarrow{\text{Glycerol kinase}}$ α-GLYCEROPHOSPHATE

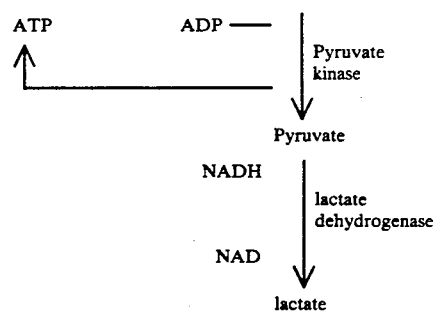

The conversion to NAD (nicotinamide adenine dinucleotide) of the reduced form NADH was measured at 340 nm. It is assumed all glycerol used up was equivalent to the amount of NAD produced and was calculated using the following equation $$\frac{\Delta \text{Absorption} \times \text{dilution factor}}{NADH \text{ extinction coefficient (6.22)}} =$$

mM Glycerol released during incubation period

Gel Filtration Exclusion Chromatography

In some cases, effluent fractions from the DEAE cellulose column that possessed significant lipolytic activity were concentrated by vacuum dialysis and the concentrate was then applied to a Sephadex G150 column (column size 1 6×30.0 cm). The column was equilibrated with 0.01M phosphate buffer pH 8.0 and active material was eluted with the same buffer. At a flow rate of about 15.0 ml/hr the effluent was collected in 1 ml fractions and the lipolytic activity of each fraction was measured as described earlier.

To achieve a better resolution of the active peaks, the main active fractions from the above Sephadex G150 column separation stage were then generally subjected to at least one further stage of gel filtration exclusion chromatography using a column having a lower porosity such as a Sephadex G50 column or an equivalent Biogel (Trade Mark) column, e.g. Biogel P4, using a similar procedure to that detailed above. Some trials were also carried out using an even lower porosity Sephadex G25 column, but it was generally found that this grade of filtration gel was not effective in retaining any appreciable amount of active material.

The use of a DEAE cellulose column with elution under a salt gradient is a procedure at least potentially useful as a preliminary separation stage, and has served to highlight the negative charge characteristics of the active lipolytic factor. It has been found, however, that under at least certain conditions eluting from the DEAE cellulose column can be rather inefficient for recovering the bound active material, especially with large sample volumes, and that this preliminary stage can in any case generally be advantageously omitted. It is therefore now usually preferred to separate the active lipolytic material by the use of Sephadex column gel filtration exclusion chromatography or the like applied directly to the samples in which the material is contained. Moreover, especially for the purpose of merely identifying the presence of the lipolytic factor material, in body fluids for example, it has been found that it is often sufficient to use only a Sephadex G50 column in a single separation stage.

In order to determine fairly accurate molecular weights for the peaks obtained in the exclusion chromatography, the columns used were calibrated with known molecular weight standards as markers.

In some cases, high performance liquid chromatography (HPLC) methods have also been used employing hydrophobic chromatography columns such as C4 butyl columns. In a typical example of using this method, the column would be run on a 30 minute gradient of 10 to 60% acetonitrile:$H_2O$/TFA(0.1%) with a run rate of 0.2ml/min.

Patients samples

For analysing blood plasma or serum samples, blood was usually removed from patients, allowed to clot at room temperature (approx. 10 min), and centrifuged immediately. Separated serum was generally stored at −20° C. until use.

In a first procedure, used in early experiments, a 1.0 ml sample of plasma or serum was applied to a DEAE cellulose column as referred to previously and the preliminary fractionation procedure was followed as already described in connection with tumour extracts. Again the active fractions from this DEAE cellulose column were then subjected to Sephadex gel filtration, generally in a single stage using a Sephadex G50 column and following the same routine as has also been described (see above), thereby further to purify the material and to determine molecular weights of active peaks. Control serum samples from non-tumour bearing individuals were also analysed for comparison.

In a second procedure which is simpler and now generally preferred, a sample (1.0 ml) of plasma, serum or urine was passed directly down a Sephadex G50 column (column size 1.6×30.0 cm). The column was equilibrated with 0.01M phosphate buffer, pH 8.0, and active material eluted with the same buffer. Void volume was determined using dextran blue and was equal to 16.0–19.0 ml depending on the age of the column. In this preferred procedure, the flow rate was 15 ml/hr and the effluent was collected in 1.0 ml fractions, 0.5 ml being then assayed for lipolytic activity. Plasma samples from Alzheimers patients (see later) were assayed invididually and then 18.0 ml of combined plasma from these patients was lyophilized and the concentrate (0.4 ml) was then applied to a Sephadex G50 column. The same method was used for any other large volume samples assayed.

BRIEF DESCRIPTION OF THE DRAWINGS

In connection with the illustrative examples detailed below reference should be made to the accompanying drawings in which.

EXAMPLE 1

A sample (1.0 ml), containing 1.3 mg protein, of an extract freshly prepared as hereinbefore described from MAC16 adenocarcinoma tumour tissue excised from an NMRI mouse with weight loss was subjected to DEAE cellulose chromatographic separation, eluting with 0.01M phosphate buffer at pH 8.0 over a range of ionic strength values provided by a linear salt gradient of 0 to 0.2M NaCl, as has also been described. The fractions of the column effluent collected were each subjected to the lipolytic assaying method already explained and the results are shown in the distribution pattern diagram of FIG. 1. This diagram shows that over a particular range of ionic strengths (salt gradient from about 0.08M to 0.2M NaCl) the fractions of effluent gave four successive major peaks of lipolytic activity. For each of the regions defining these four peaks of activity the respective fraction or fractions were then concentrated by vacuum dialysis and subjected to gel filtration exclusion chromatography separation, again as already described, using initially a Sephadex G150 column (void volume 23.0 ml). Measurements of the lipolytic activity of the fractions of effluent obtained in this separation stage then gave the results shown in FIG. 2 from which it will be seen that major activity was concentrated in a relatively narrow range characterised by two adjacent strong peaks estimated, from their position, to be representative of material or substances having molecular weights less than 5000 daltons and generally of the order of 3000 daltons and 1500 daltons respectively. These results were virtually the same irrespective of whether the DEAE cellulose fractions put through the Sephadex G150 column were from the region of the first active peak, the second active peak, the third active peak or the fourth active peak of the distribution pattern of FIG. 1.

The fractions of the first stage Sephadex G150 column effluent producing the first of the two activity peaks shown in FIG. 2 were then subjected again to gel filtration exclusion chromatography separation using this time a lower porosity Sephadex G50 column (void volume 17.0 ml). The results that were then obtained from the measurements of the lipolytic activity of the column effluent fractions are presented in FIG. 3 which shows that the activity distribution pattern now displays three distinct main peaks. This procedure was also repeated for the fractions of the first Sephadex column effluent producing the second of the two activity peaks shown in FIG. 2, and the results are shown in FIG. 4 from which it will be seen that the activity distribution pattern in this case displays only one main peak.

Figure 3:
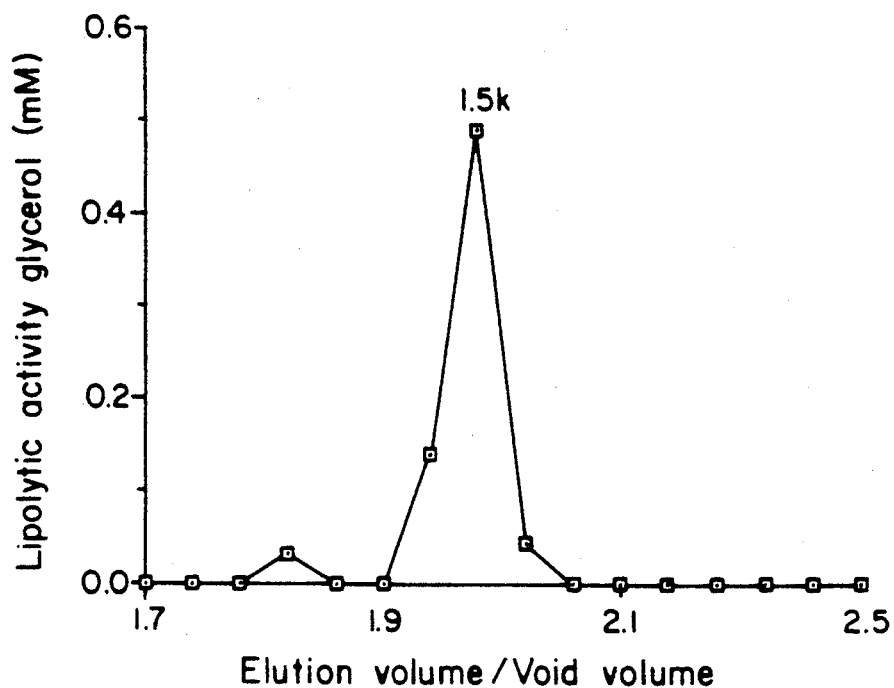
FIG. 3 is a diagram of the lipolytic activity distribution pattern of fractions obtained by a further stage of gel filtration on a Sephadex G50 column of those fractions from the first gel filtration stage illustrated in FIG. 2 that contained the first major activity peak (SG50 chromatography of peak 21 of SG150 active fractions)
Figure 4:
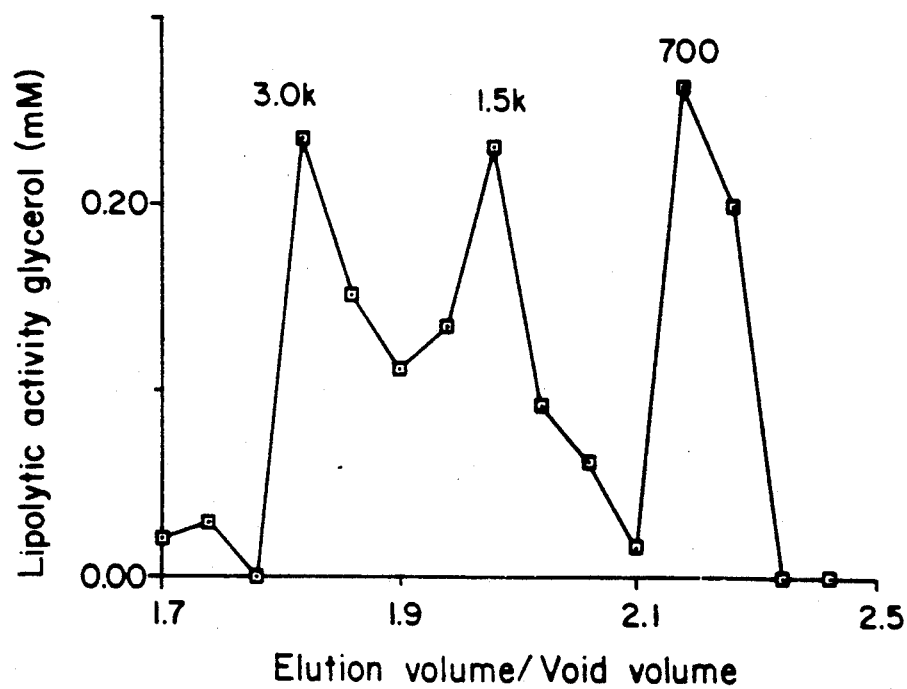
FIG. 4 is a diagram of the lipolytic activity distribution pattern of fractions obtained by a further stage of gel filtration on a Sephadex G50 column of those fractions from the first gel filtration stage illustrated in FIG. 2 that contained the second major activity peak (SG50 chromatography of peak 1 of SG150 active fractions).
Figure 5:
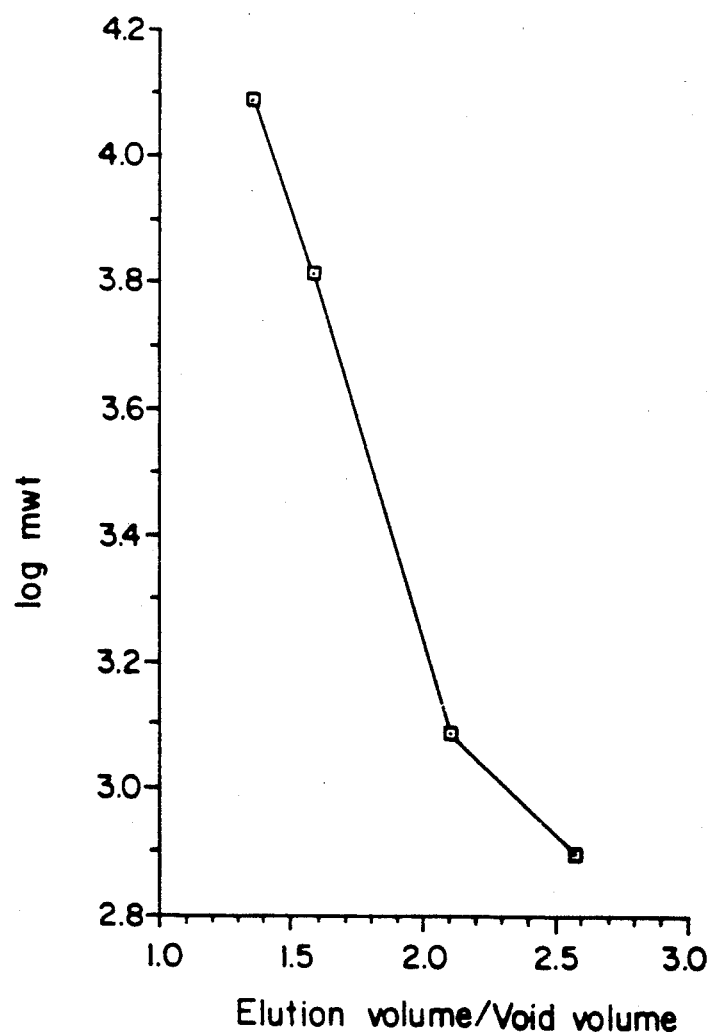
FIG. 5 is a diagram showing a calibration chart of the Sephadex G50 column used in the gel filtration separations (Calibration graph of the Sephadex G50 column)

The Sephadex G50 column used in obtaining the results of FIGS. 3 and 4 was calibrated using, as molecular weight standards, Cytochrome C (M.W. of 12,400), Aprotinin (M.W. of 6,600), Actinomycin D (M.W. of 1,247) and Rifampicin (M.W. of 834), the calibration chart produced being illustrated in FIG. 5.

By comparison with this calibration chart, it has been deduced that the three main activity peaks shown in FIG. 3 represent material or substances having respective molecular weights of about 3,000 daltons, 1,500 daltons and 700 daltons, whilst the single main activity peak shown in FIG. 4 represents a material or substance having a molecular weight of about 1500 daltons. It is believed that the molecular weight values determined by this technique are generally accurate to within about ±at least 200 daltons.

Figure 1:
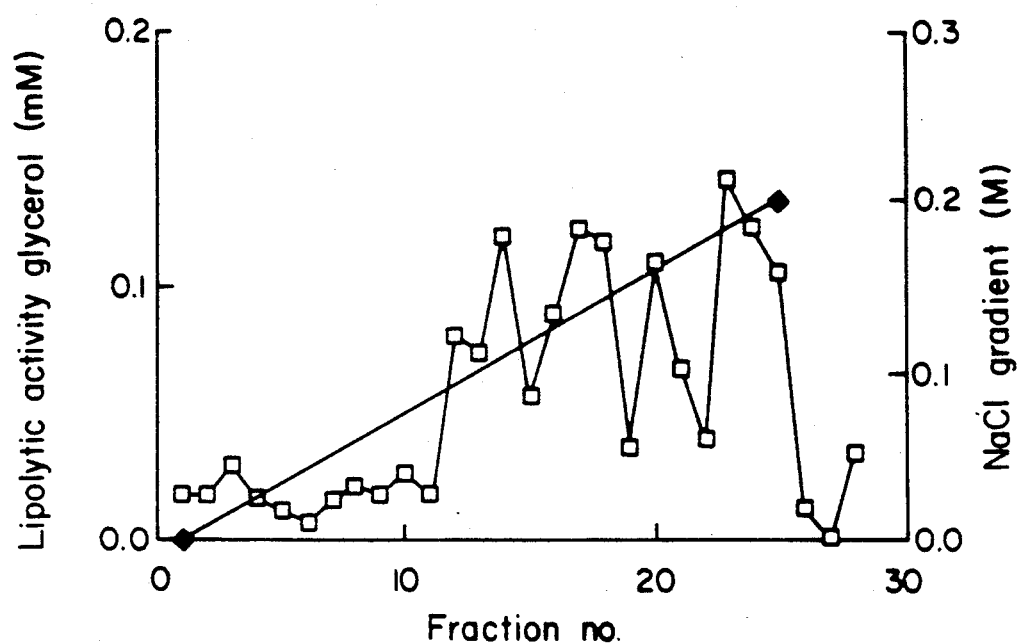
FIG. 1 is a diagram of the lipolytic activity distribution pattern of fractions obtained by DEAE cellulose chromatography of a sample from an extract of a MAC16 adenocarcinoma (DEAE cellulose chromatography of a sample (1.0 ml) from an extract of the MAC16 adenocarcinoma)
Figure 2:
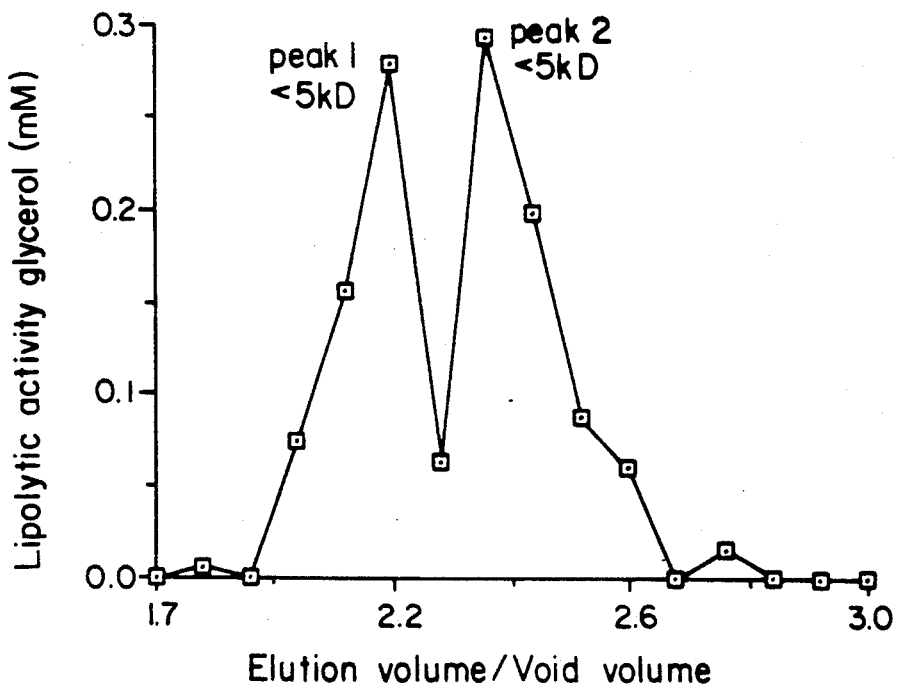
FIG. 2 is a diagram of the lipolytic activity distribution pattern, showing two major activity peaks, of fractions obtained in a first stage of gel filtration exclusion chromatography, using a Sephadex G150 column, applied to the active lipolytic fractions obtained from the DEAE cellulose chromatographic separation illustrated in FIG. 1 (SG150 chromatography of DEAE active fractions from the MAC16 tumour)
Figure 6:
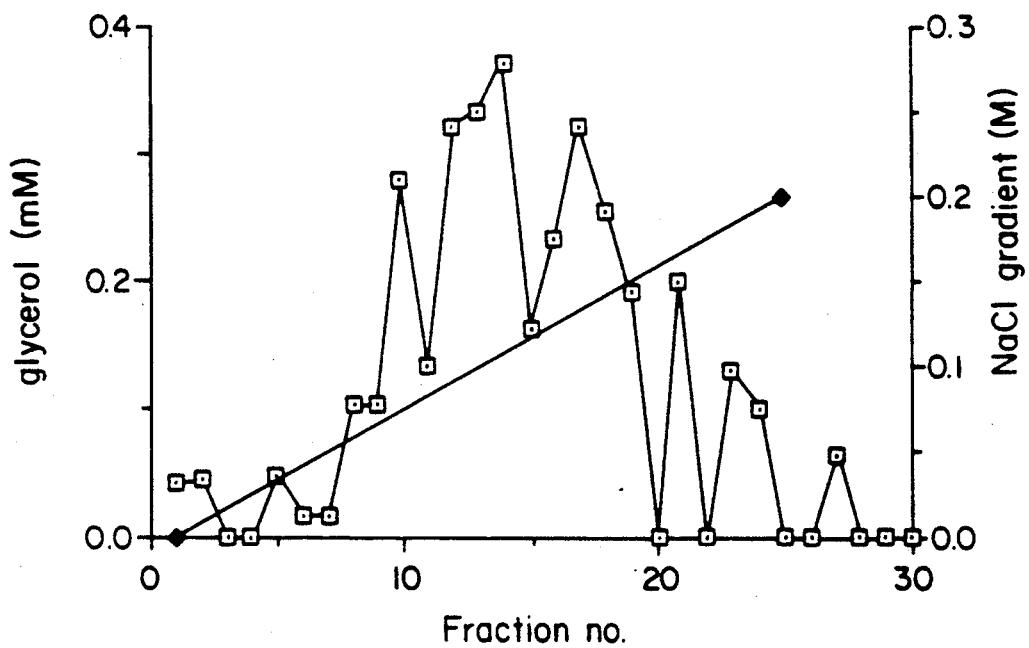
FIG. 6 is a diagram similar to FIG. 1 but showing the lipolytic activity distribution pattern of fractions obtained by DEAE cellulose chromatography of a sample of more concentrated extract from a MAC13 adenocarcinoma (DEAE cellulose chromatography of a (concentrated) sample of an extract of from the MAC13 adenocarcinoma)
Figure 7:
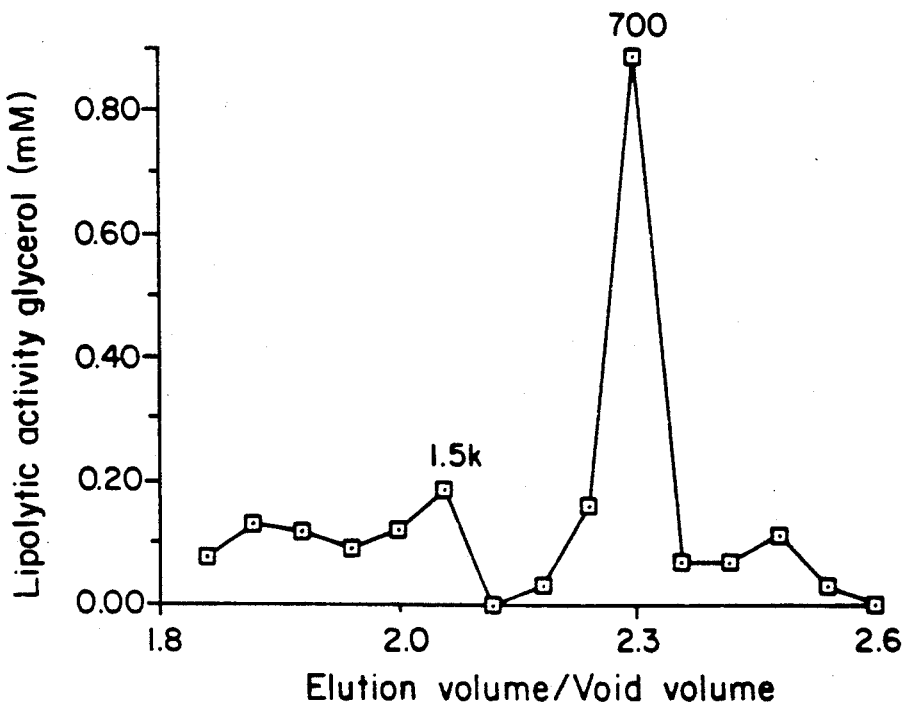
FIG. 7 is a diagram of the lipolytic activity distribution pattern of fractions obtained from gel filtration, using a Sephadex G50 column, of those active lipolytic fractions obtained from the DEAE cellulose separation that contained the major activity peaks illustrated in FIG. 6 from the MAC13 adenocarcinoma (SG50 chromatography of a sample (0.1 ml) of the MAC13 tumour homogenate).

These results were found to be consistent and fully reproducible upon repeating the procedure in respect of other sample preparations of extracts from MAC16 tumour tissue. In addition, a DEAE cellulose chromatographic separation method similar to that described above but using a small DEAE cellulose column 12cm long was also applied to an extract from a MAC13 adenocarcinoma. This tumour (obtained from Dr. J. A. Double, University of Bradford, U.K.) is related to the MAC16 adenocarcinoma but is of a different cell line. Although it has not been found to produce symptoms of cachexia when growing in mice, extracts of the tumour do show a certain level of lipolytic activity, albeit that this is considerably less than that usually obtained with a MAC16 tumour (see reference 2). However, the MAC13 tumour extract tested in this case was prepared at a concentration ten-fold that of an extract from the MAC16 tumour tested under the same conditions and a sample containing 4.0 mg/ml protein was applied to the small DEAE cellulose column. Otherwise, the DEAE cellulose chromatographic separation was carried out as already described above in connection with the MAC16 tumour extracts, and the results are shown in FIG. 6. A similarity between FIG. 6 and FIG. 1 is immediately apparent, especially insofar as the fractions obtained again give peaks of lipolytic activity eluting at the same or very similar ionic strengths as those for the MAC16 tumour extracts. The fractions giving these main activity peaks were then subjected to a single stage of Sephadex gel filtration using a calibrated Sephadex G50 column, also as before, and the results are illustrated in FIG. 7. Again, it will be seen, peaks indicating active components having molecular weights of about 700 daltons and 1500 daltons were obtained.

The conclusion from these preliminary results is that other tumours also produce in detectable quantities the same lipolytic factor, or active components thereof, as is produced by the MAC16 adenocarcinoma, even although there may be no obvious symptoms of cachexia. This has been confirmed in various other experiments.

EXAMPLE 2

In a further set of experiments, samples (1.0 ml) of tumour homogenate or cell culture extracts or of body fluids such as blood plasma, serum or urine from mice were applied direct to a Sephadex G50 column without a preliminary stage of fractionation using a DEAE cellulose column.

Figure 8:
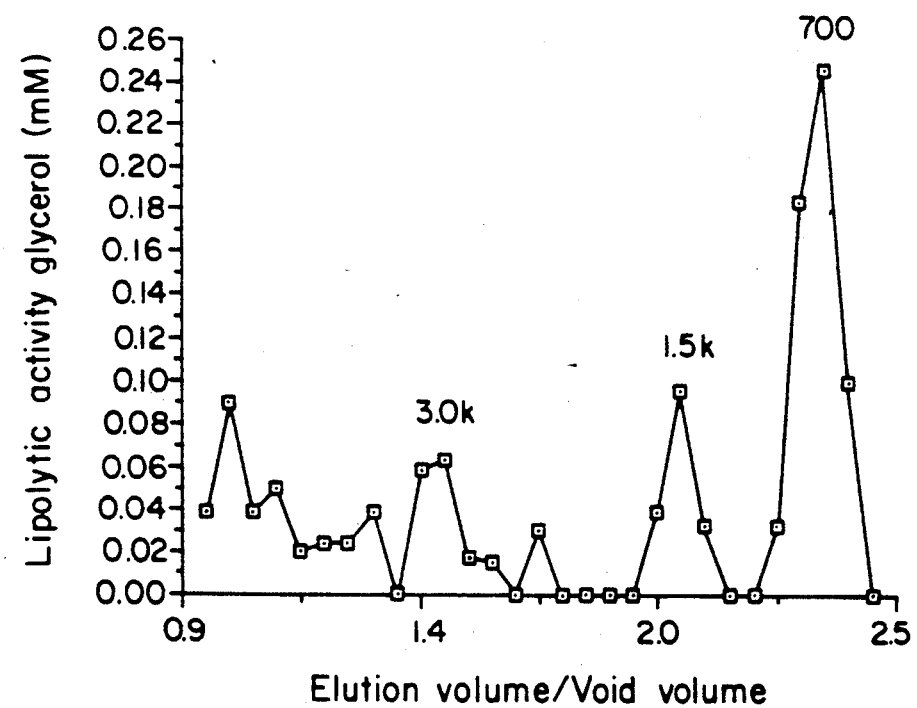
FIG. 8 is a diagram of the lipolytic activity distribution pattern of fractions obtained by direct gel filtration using a Sephadex G50 column applied to a sample of a MAC16 tumour homogenate extract (SG50 chromatography of a sample, (0.1 ml) of MAC16 tumour homogenate)

Using this modified procedure for an extract from a MAC16 tumour homogenate prepared as previously described, the characteristic lipolytic activity distribution pattern with three distinct main peaks representative of substances having molecular weights of about 700, 1500 and 3000 daltons respectively was again obtained, as illustrated in FIG. 8.

Figure 9A:
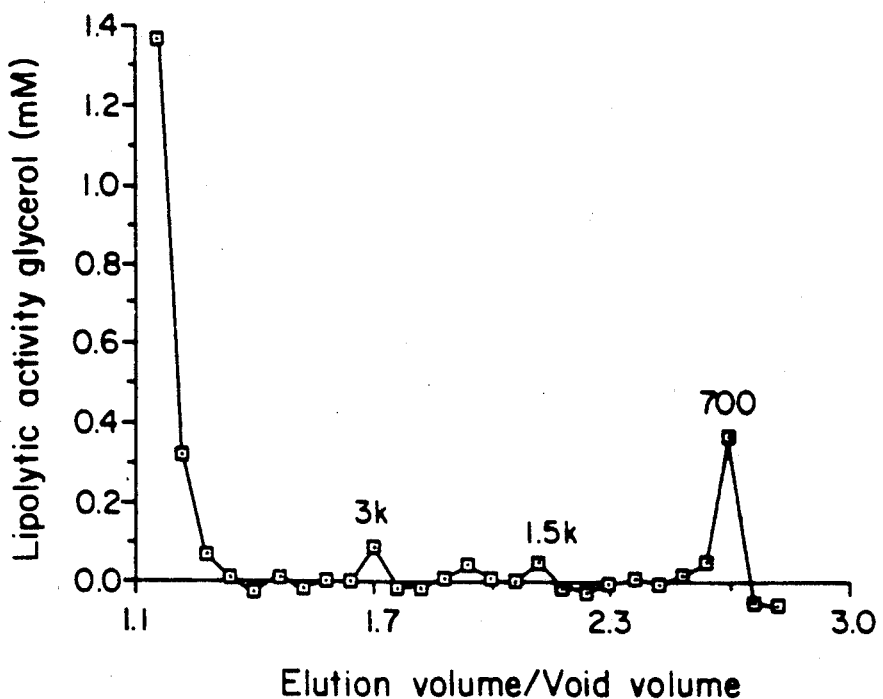
FIGS. 9a, 9b and 10 are diagrams similar to FIG. 8 but showing the activity distribution patterns of fractions obtained by direct Sephadex G50 column gel filtration of urine samples from mice bearing MAC16 and MAC13 tumours respectively (MG50 chromatography of a sample (0.1 ml) of MAC16 urine, SG50 chromatography of Fraction 17)high mwt sp) from MAC16 urine, and SG50 chromatography of a sample (1.0 ml) of urine from mice bearing a MAC13 tumour, respectively)
Figure 9B:
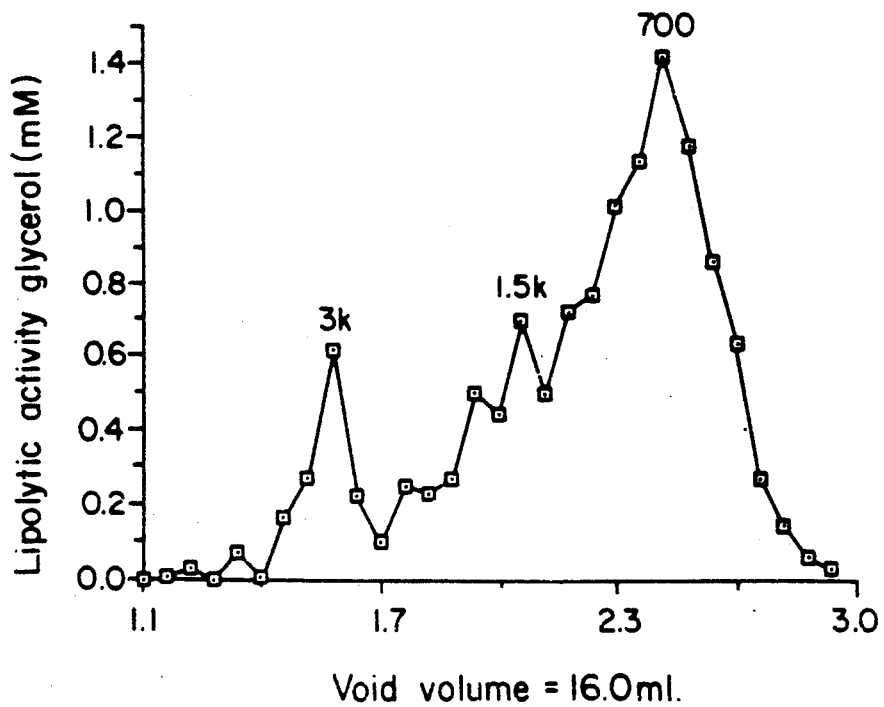
Figure 10:
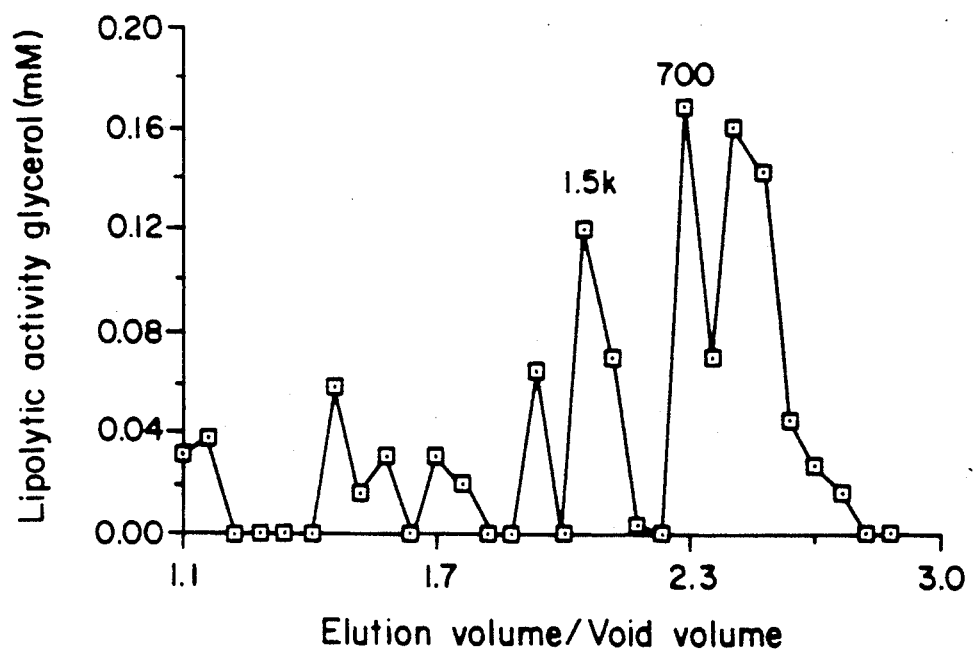
Figure 11:
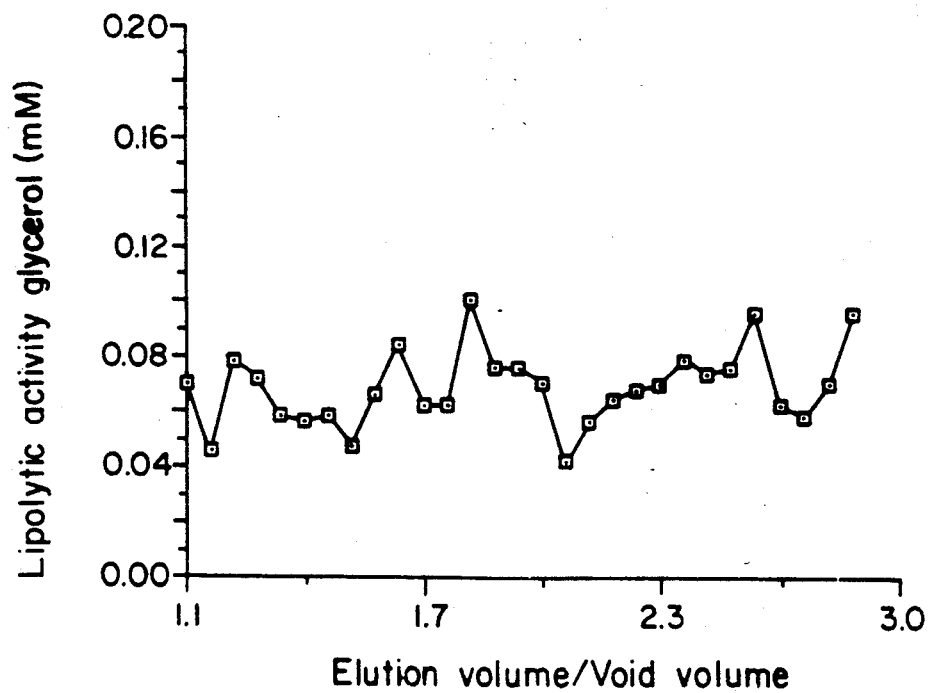
FIG. 11 is a similar diagram showing the pattern obtained under the same conditions in respect of a urine sample from a healthy non-tumour bearing mouse used as a control (SG50 chromatography of a sample (1.0 ml) of urine from a non-tumour bearing mouse (NMRI)

The same peaks of this activity distribution pattern could also be detected in samples of urine from mice bearing either MAC16 or MAC13 tumours, even although sometimes there was a somewhat more variable background of other peaks and variations in the relative heights of the peaks. This is shown in FIGS. 9a and 10 which may be compared with the corresponding distribution pattern obtained with a sample of urine from a non-tumour bearing mouse shown in FIG. 11 (note differences in scale). FIG. 9b shows the corresponding pattern obtained when a sample from the apparent very high molecular weight fraction at the left of FIG. 9a was reapplied to the Sephadex G50 column.

EXAMPLE 3

Evidence of the effectiveness of the active lipolytic factor in producing weight loss was obtained by administering purified samples of the active substance to both non-tumour bearing and tumour bearing mice, the latter generally being selected for absence of symptoms of cachexia.

For this purpose, purified samples of the active substance were prepared from MAC16 tumour tissue culture medium using a Sephadex G-150 column in a first separation stage followed by combining the most active fractions and refractionating on a Biogel P4 column, after which the most active fractions were again combined and lyophilized before finally being subjected to a stage of hydrophobic chromatography using a $C_{18}$ "Sep-Pack" (Trade Mark) column. Active fractions from this last stage were then used to prepare samples for intraperitoneal administration, by injection, to NMRI mice employed as test animals.

In carrying out a series of tests, the average activity of the samples injected was such that 100 $\mu$l caused 0.1 mM glycerol release when incubated with mouse adipose tissue. Two sets of control experiments were also run—in one set no injections were given, and in the other set a corresponding amount of normal saline was injected instead of samples of the active factor, under exactly the same conditions, thereby to obtain comparitive measurements to account for any stress-induced weight loss.

Figure 12:
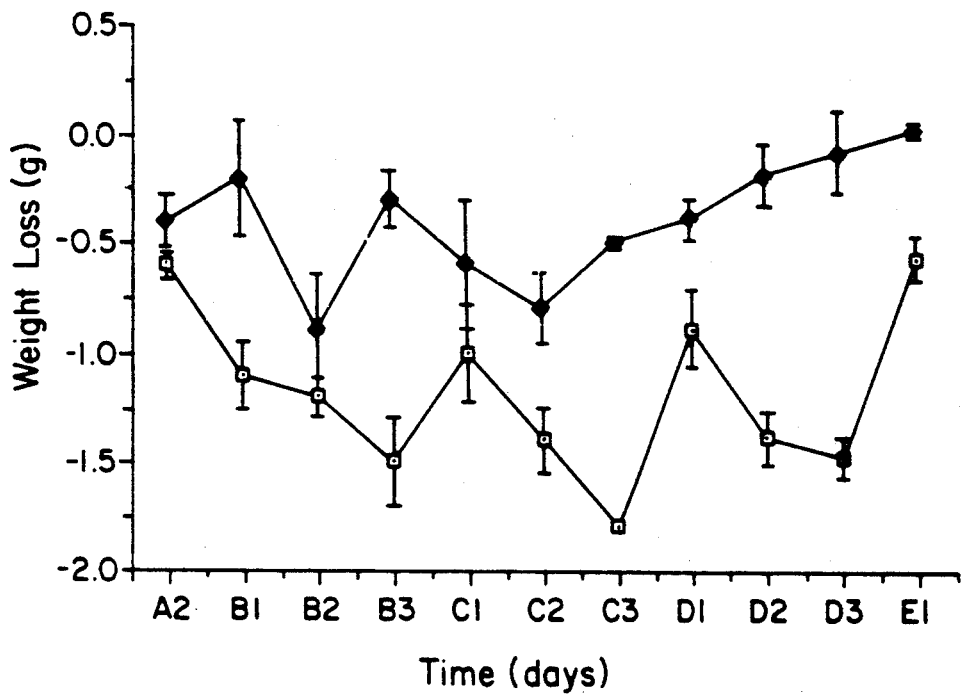
FIG. 12 is a diagram illustrating the effect of administration of the active lipolytic factor in producing weight loss in healthy non-tumour bearing mice (effect of lipolytic factor on non-tumour bearing NMRi mice)

In conducting these tests, the injections were generally given three times a day, at which times the body weights were also measured, and the averaged results in respect of administering the active lipolytic substance in this manner to groups of non-tumour bearing NMRI mice are illustrated in the diagram of FIG. 12. In this diagram, A, B, C, D etc represent different successive days and the top curve is the control in which only saline was injected. During this period, the mice which were not injected at all showed no significant weight changes.

Although overnight, after feeding, there was generally some restoration of weight loss, it will be seen from the lower curve that administration of the active lipolytic factor was effective overall to produce very significant weight loss in the animals without significant reduction of food or fluid intake.

Figure 14:
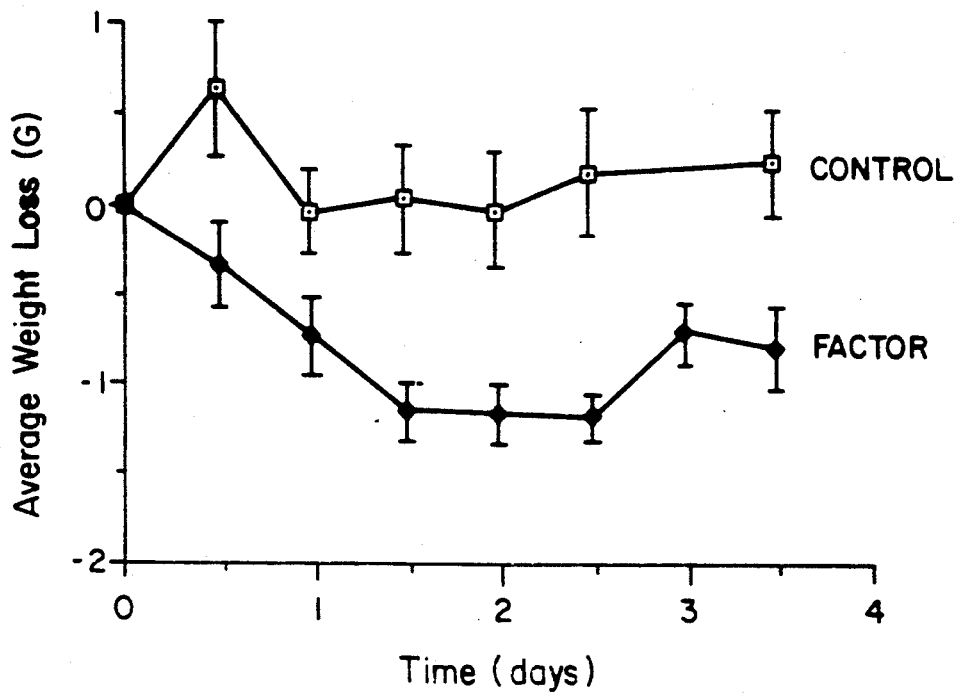
FIGS. 13a, 13b and 14 are diagrams similar to FIG. 12 but showing respectively the weight loss effects produced in non-cachetic MAC16 and MAC13 tumour bearing mice (effect of Lipolytic Factor on MAC 16 Tumour Bearing Mice, Effect of Factor on Weight Loss in MAC 13 Tumour bearing NMR I Mice, and IP injection of factor and L1210 control into MAC13 Mice, respectively)
Figure 13A:
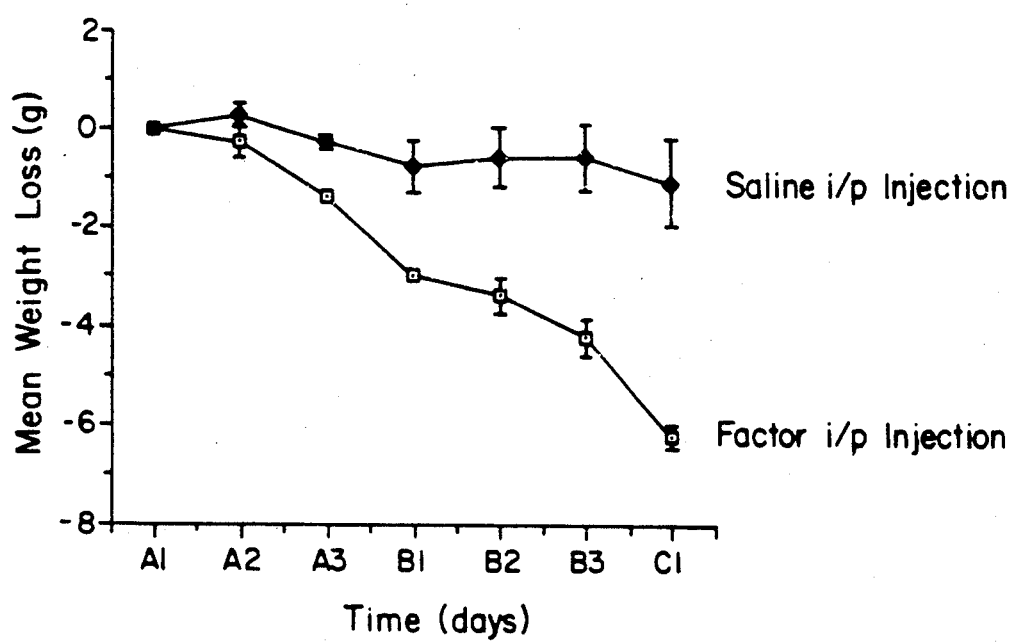
Figure 13B:
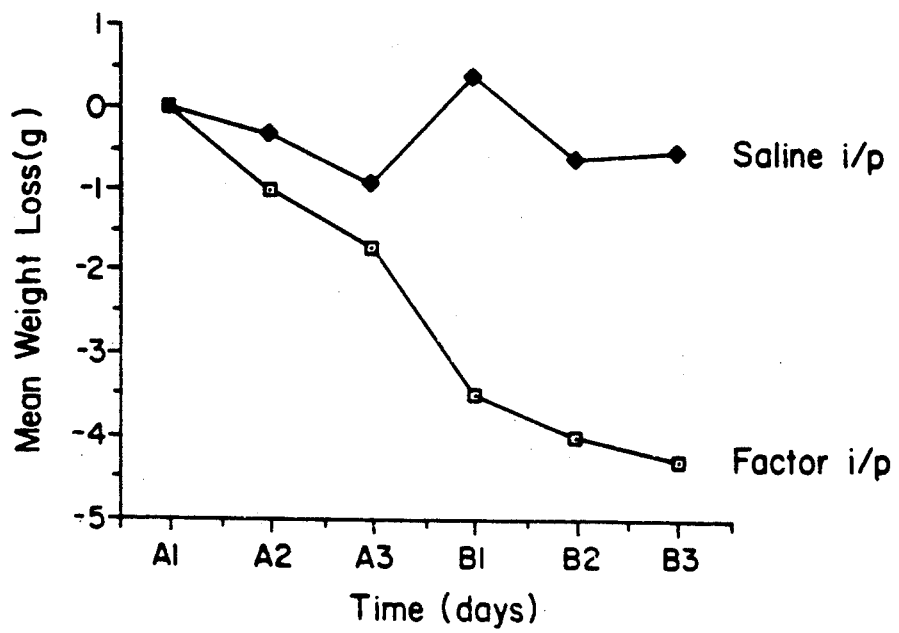

In the corresponding series of tests carried out using MAC16 tumour bearing NMRI mice selected for minimal symptoms of cachexia or using non-cachectic MAC13 tumour bearing NMRI mice, further weight loss effects were observed after administering the active lipolytic factor, as illustrated in the diagrams of FIGS. 13a, 13b and 14. The weight loss effects were also found to be dependent on dosage amounts. Provided doses were not too high the weight loss effects could be sustained without reduction in food or fluid intake, this being the situation that produced FIG. 14.

These results and other work, including results obtainable on administering the lipolytic factor to animals afflicted with a condition of obesity, show that preparations of the purified or partially purified lipolytic factor have at least a potential therapeutic value for use in the controlled treatment of this condition in mammals, including humans. For this purpose, especially for the controlled treatment of obesity in humans, either for medical reasons or cosmetic reasons, therapeutically useful quantities of the essentially pure active substance can be made up into pharmaceutical formulations for administration, subject to Health Regulations approval, in any suitable manner, e.g. parenterally or orally. Such formulations may be presented in unit dosage form and may comprise a pharmaceutical composition, prepared by any of the methods well known in the art of pharmacy, in which a preparation of the active lipolytic substance is combined in intimate association or admixture with any other suitable ingredient providing a compatible pharmaceutically acceptable carrier, diluent or excipient. For parenteral administration the formulations may comprise sterile liquid preparations of a predetermined amount of the active lipolytic substance contained in ampoules ready for use.

EXAMPLE 4

As hereinbefore mentioned, tests on body fluids such as blood plasma and serum or urine from cancer patients, especially but not exclusively patients with symptoms of cancer cacheria, have also been found to show abnormal elevated lipolytic activity.

Figure 17:
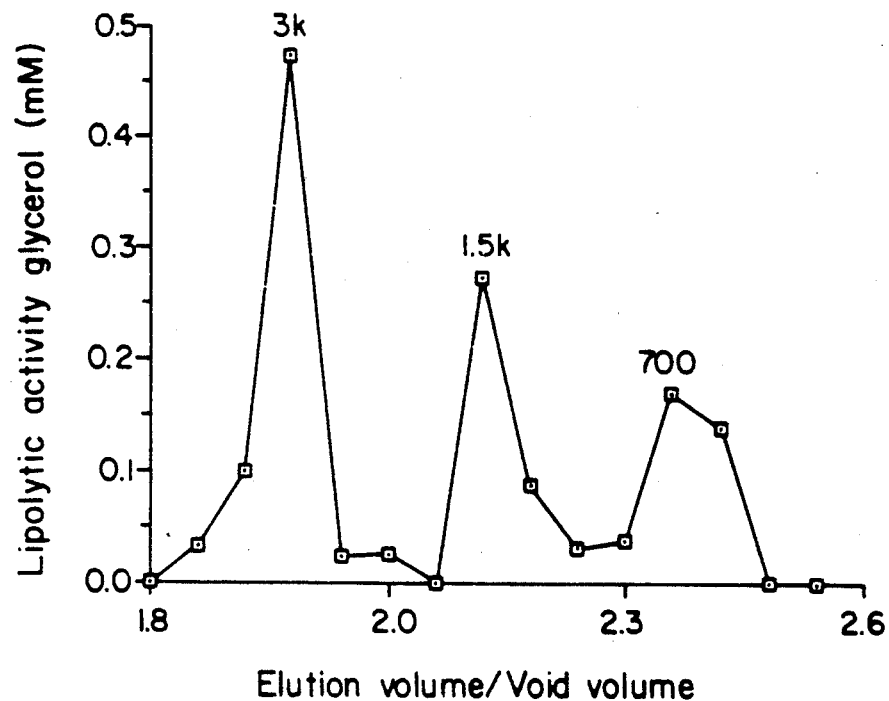
FIG. 17 is a diagram of the lipolytic activity distribution pattern of fractions obtained from gel filtration, using a Sephadex G50 column, applied to those active lipolytic fractions of the serum, obtained from the DEAE cellulose column separation, that contained the first major activity peak illustrated in FIG. 15 (SG50 chromatography of patient (A.H.) peak 1 from DEAE active fractions)
Figure 18:
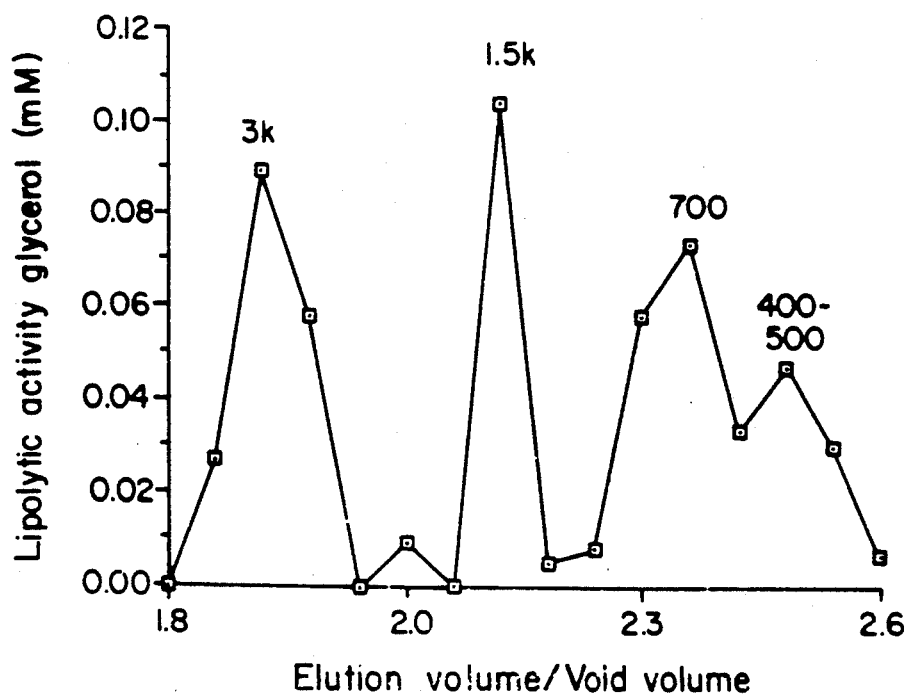
FIG. 18 is a diagram of the lipolytic activity distribution pattern of fractions obtained from gel filtration, using a Sephadex G50 column, applied to those active lipolytic fractions of the serum, obtained from the DEAE cellulose column separation, that contained the second major activity peak illustrated in FIG. 15 (SG50 chromatography of patient A.H) peak 2 from DEAE active fractions)

By way of example, a summary of data obtained from one group of such patients at the Queen Elizabeth Hospital in Birmingham (U.K.) is shown in Table 1. Plasma or serum samples obtained from these patients were subjected to DEAE cellulose chromatographic separation, followed by a single stage of gel filtration exclusion chromatography of the most active fractions using a Sephadex G50 column. Apart from this direct use of the G50 column in a single stage of gel filtration, the chromatographic procedures followed were the same as described in connection with the MAC16 tumour extracts in Example 1. The results are typified by the diagrams of the lipolytic activity distribution patterns for one particular patient which are shown in FIGS. 15, 17 and 18.

Figure 15:
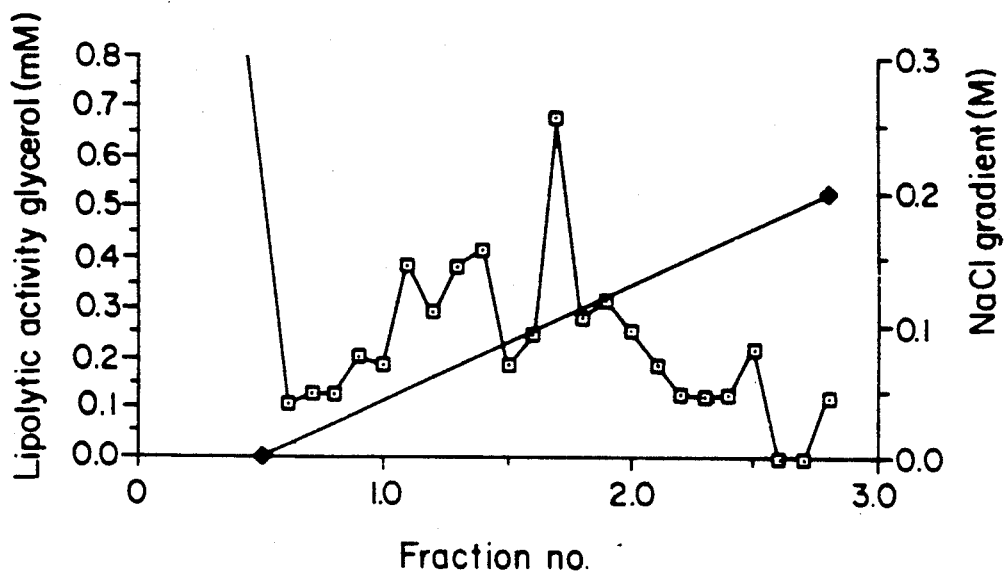
FIG. 15 is a diagram of the lipolytic activity distribution pattern of fractions obtained by DEAE cellulose chromatography of a sample of serum from a human cancer patient (DEAE cellulose chromatography of a serum sample (1.0 ml) from a cancer patient (A.H))

It will be seen from FIG. 15 that the activity distribution pattern measured after the DEAE cellulose

TABLE 1

| | | | Plasma lipolytic activity in untreated, weight losing cancer patients. | | | | |
|---|---|---|---|---|---|---|---|
| Patient | Sex | Age | Tumour type | Wt loss kg | Food intake | Blood glucose | Lipolytic activity moles glycerol/ ml/plasma |
| J. V. | Male | 70 | Prostate | −13.9 | decreased | 6.4 | 0.227 |
| R. U. | Female | 56 | Ovary | +4.0 | decreased | — | 0.061 |
| S. K. | Male | 71 | Prostate | −4.0 | normal | 5.4 | 0.140 |
| G. P. | Female | 66 | Ovary or pancreas | −7.7 | normal | — | 0.087 |
| J. K. | Female | 60 | Breast | −12.4 | normal | — | 0.233 |
| R. D. | Male | 62 | Lung | −11.1 | normal | 4.1 | 0.370 |
| A. H. | Male | 60 | Bladder | −9.0 | decreased | — | 0.331 |
| A. M. | Female | 77 | Lymph nodes | −19.6 | normal | — | 0.359 |

Figure 16:
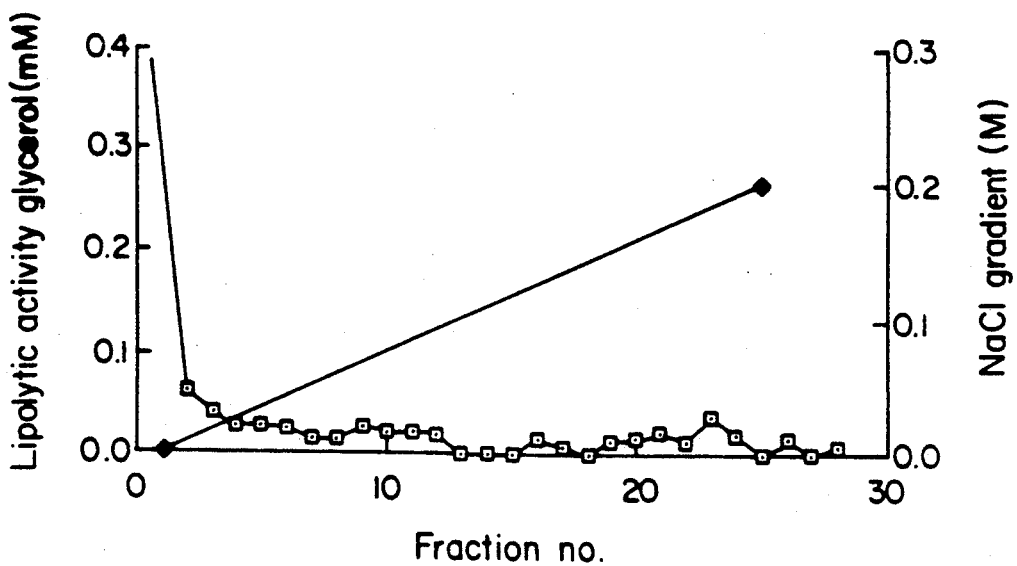
FIG. 16 is a diagram of the lipolytic activity distribution pattern of fractions obtained by DEAE cellulose chromatography of a sample of control serum from a non-tumour bearing healthy human individual (DEAE cellulose chromatography of a control serum sample from a non-tumour bearing individual (A.S.))

(Control values for lipolytic activity for normal subjects range from 0.013 to 0.077 $\mu$moles glycerol released/ml plasma.

chromatographic separation is of a form similar to that of the MAC16 tumour extracts shown in FIG. 1, especially insofar as it includes four discernible regions having peaks of activity eluting at substantially the same ionic strengths as the four major activity peaks of FIG. 1. This pattern contrasts sharply with the activity pattern, shown in FIG. 16, which was obtained on applying the same DEAE cellulose chromatographic procedure to a control sample of normal human serum; this shows minimal lipolytic activity with no corresponding distribution of peaks.

The subsequent single gel filtration stage using the Sephadex G50 column was applied separately to the effluent fractions from the DEAE cellulose column that provided, respectively, the first and the second main peaks of lipolytic activity shown in FIG. 15. The column was calibrated for determining molecular weights as before, and the results are shown in the distribution pattern diagrams of FIGS. 17 and 18.

In the case of FIG. 17, again it will be seen that three peaks of activity were obtained corresponding to material or substances having molecular weights of approximately 3,000 daltons, 1,500 daltons and 700 daltons, exactly as in the distribution pattern of FIG. 3. In the case of FIG. 18, there are again peaks corresponding almost exactly to components having respective molecular weights of approximately 1,500 and 700 daltons, and there is also a first peak that corresponds to a molecular weight of approximately 3,000 daltons together with an additional fourth peak corresponding to a molecular weight of about 400–500 daltons. In any event, the close correspondence between the results from the MAC16 tumour extracts and the serum samples from cancer patients is very striking, demonstrating that in both cases there is an active lipolytic substance comprising the same molecular species or active molecular groupings, perhaps with only minor homological differences between the murine and human species.

EXAMPLE 5

The close correspondence between the results from testing MAC tumour bearing mice and those from cancer patients, and the relationship between the presence of the particular lipolytic substance or factor herein identified and the presence of a tumour or cancer, is further dramatically illustrated by testing of urine samples.

The fact that urine samples of cancer patients, at least untreated weight losing patients, generally possess some abnormal elevated level of lipolytic activity is illustrated for example by the data presented in Table 2 obtained for a group of such patients. Similar data has been obtained for other larger groups of patients.

Many such urine samples were subjected to a single stage of gel filtration exclusion chromatography using a Sephadex G50 column generally in accordance with the procedure already described and as employed previously in Example 2.

Figure 19:
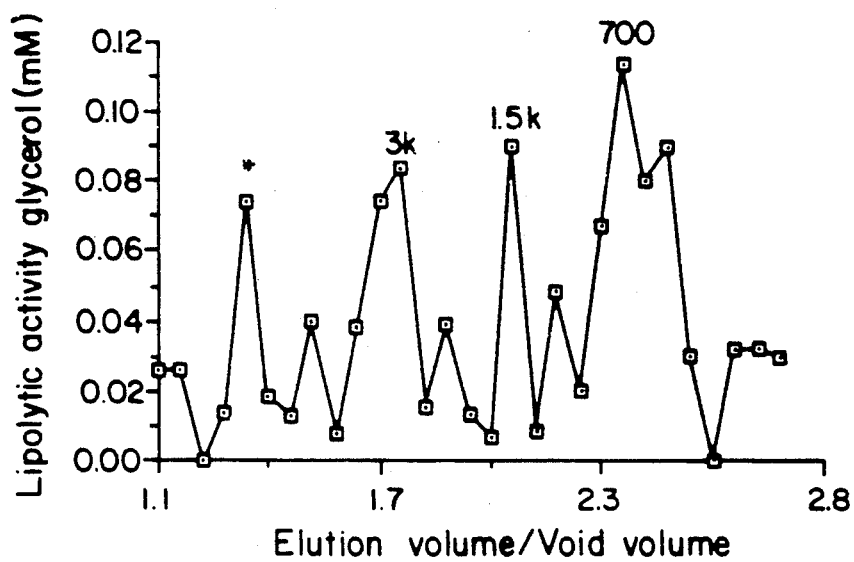
FIG. 19 is a diagram of the lipolytic activity distribution pattern of fractions obtained by direct gel filtration using a Sephadex G50 columns for a urine sample from a cancer patient with weight loss (SG50 chromatography of a sample (100 ml) of urine from a cancer patient (R) with weight loss)
Figure 20:
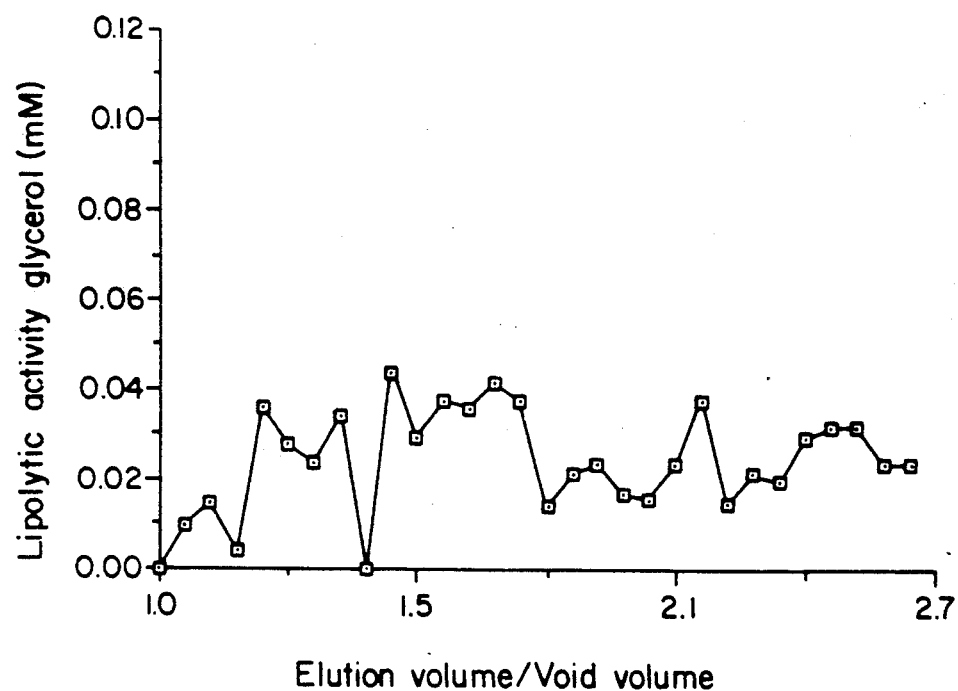
FIG. 20 is a diagram similar to FIG. 19 but showing the results obtained for a urine sample from a healthy control subject (SG50 chromatography of a sample (1.0 ml) of urine from a control subject (A.S))

By way of example, the results obtained for a urine sample (100 ml) from one cancer patient with weight loss are shown in the diagram of FIG. 19, whilst for comparison FIG. 20 is a similar diagram showing the results obtained in the same way for a urine sample from a healthy control subject. Although the fractions obtained can be seen to give a somewhat variable background of minor peaks of lipolytic activity, again in

TABLE 3

| Lipolytic activities of human colon tumours | | | | |
|---|---|---|---|---|
| Patient | Sex | Age | Weight Loss (kg) | Lipolytic activity μmol glycerol/ mg protei |
| P | female | 61 | none | 1.10 ± 0.20 |
| H | male | 86 | 6.4 | 0.80 ± 0.20 |
| R. E | male | | | 2.30 ± 0.30 |
| A | male | 62 | none | 1.20 ± 0.30 |
| B. C | female | 68 | none | 1.00 ± 0.30 |
| B. C (normal tissue) | | | | 0.50 ± 0.10 |
| M | male | 68 | none | 1.00 ± 0.20 |
| M (normal tissue) | | | | 0.07 ± 0.04 |
| MAC16 mouse colon adenocarcinoma | | | | 0.570 ± 0.500 |
| mouse (normal colon tissue) | | | | 0.021 ± 0.004 |

FIG. 19 the characteristic lipolytic activity distribution pattern previously noted, with three distinct main peaks representative of substances having molecular weights of about 750 (nearer 700 as measured in this instance), 1500 and 3000 daltons respectively, is clearly apparent, together in this particular case with another additional fairly strong peak at a position corresponding to a species of somewhat higher molecular weight. In contrast, in FIG. 20 there is no corresponding characteristic distribution pattern discernible or main peaks apparent at any of the three above-mentioned molecular weight values.

Figure 22:
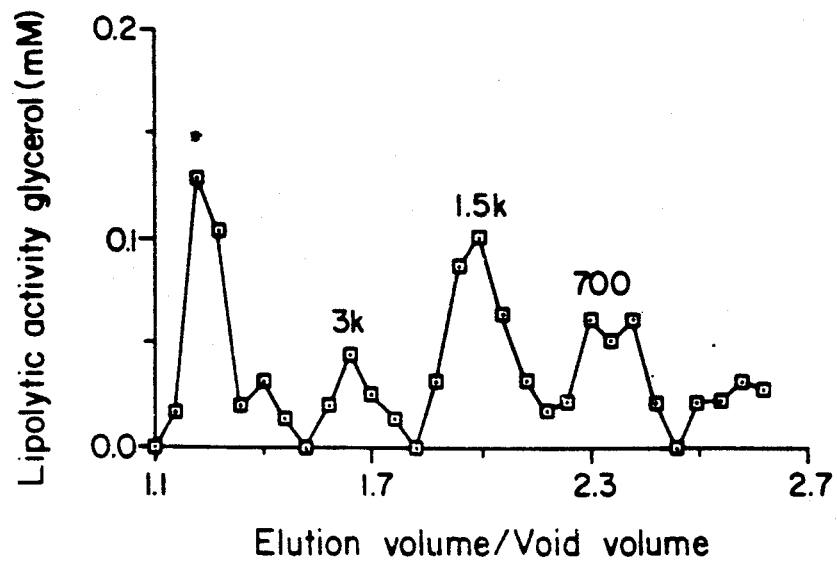
FIGS. 21 and 22 are further diagrams similar to FIG. 19 but showing the results obtained in the same way for urine samples from two other cancer patients having different types of cancer but without any symptoms of weight loss (G50 chromatography of a urine sample (1.0 ml) from a cancer patient (J.C.), and SG50 chromatography of a sample (100 ml) of urine from a cancer patient (P) without weight loss, respectively)
Figure 21:
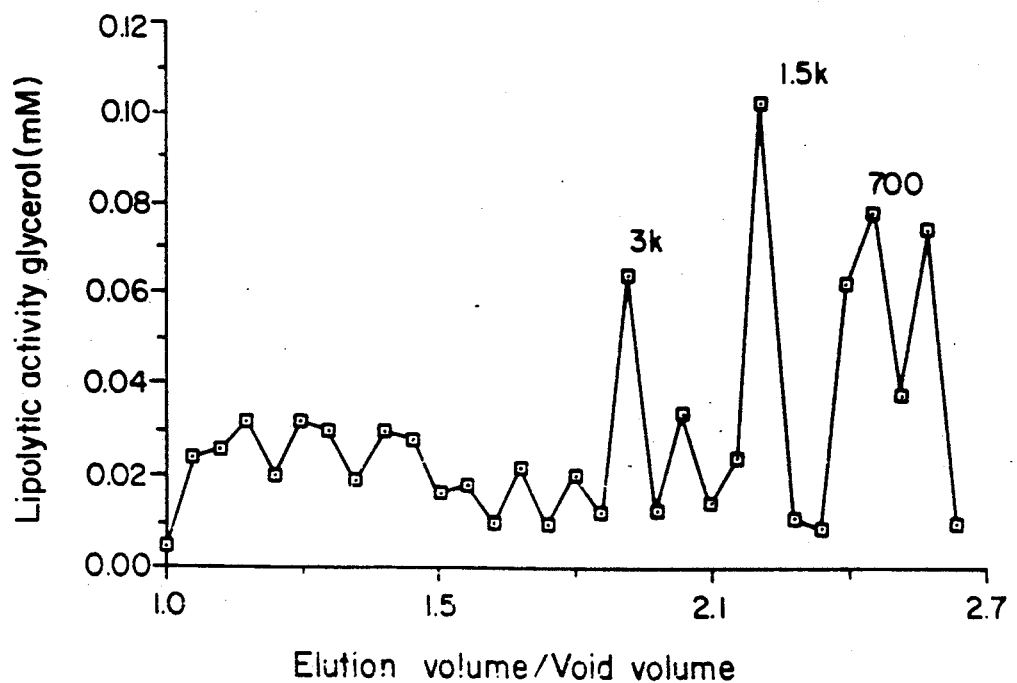

The corresponding results obtained by the same technique but using urine samples from two other cancer patients who had different types of cancers (cervical and lung cancers respectively) without symptoms of weight loss are shown by way of further example in the diagrams of FIGS. 21 and 22. Again, in both these cases and nothwithstanding the lack of weight loss or cachectic symptoms, the characteristic lipolytic activity distribution pattern with main peaks indicating active species of about 700–750, 1500 and 3000 daltons is clearly to be seen. Particularly noteworthy, also, is the fact that the results shown in FIG. 21 related to a patient having a cancer (cervical cancer) at an early operable and curable stage of development.

Using the same Sephadex G50 column technique, the presence of the same active lipolytic factor has moreover been detected in extracts from various human tumours, for example a human colon tumour (see Table 3), as well as in samples of body fluids, and overall this same lipolytic factor appears to be specifically associated with a wide range of malignant tumours, not necessarily limited to cachexia-inducing tumours, in both animals and humans. Indeed, it is now believed probable that this particular lipolytic factor of the present invention is a unique product likely to be produced at some level with most, if not with all, cancers in at least human individuals, and that where there is a cancer-associated

TABLE 2

| Urine lipolytic activity in untreated, weight losing cancer patients | | | | | | | |
|---|---|---|---|---|---|---|---|
| Patient | sex | age | tumour type | wt loss (kg) | food intake | Lipolytic activity μmol glycerol/ $10^5$ cells/ ml urine | Lipolytic activity μmol glycerol/ $10^5$ cells/ mg creatinine |
| R. D | male | 62 | lung | 9.0 | normal | 0.540 ± 0.058 | 2.18 ± 0.23 |
| J. C | female | 63 | cervical | 0 | increased | 0.563 ± 0.058 | 6.95 ± 0.72 |
| M. T | female | 62 | ovarian | 18.3 | decreased | 0.500 | — |
| E. H | male | 82 | prostate | 17.5 | normal | 0.424 ± 0.072 | 5.36 ± 1.36 |
| B. T | female | 53 | ovarian | 31.0 | decreased | 0.510 ± 0.026 | 4.43 ± 0.23 |

Figure 25A:
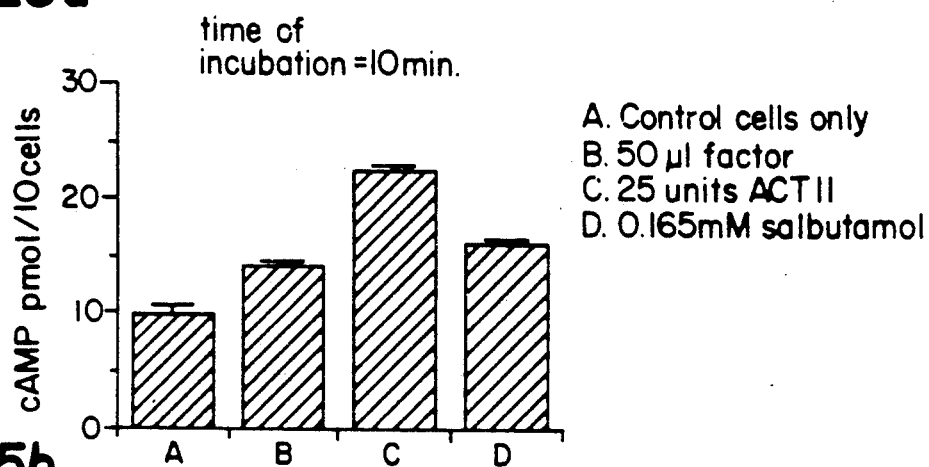
FIG. 25 is a set of bar chart diagrams (a), (b) and (c) showing the effect of the lipolytic material of the present invention on the cAMP level in fat cells and comparing this with the effect of other lipolytic agents (Effect of factor, ACTH salbutamol on CAMP levels)
Figure 25B:
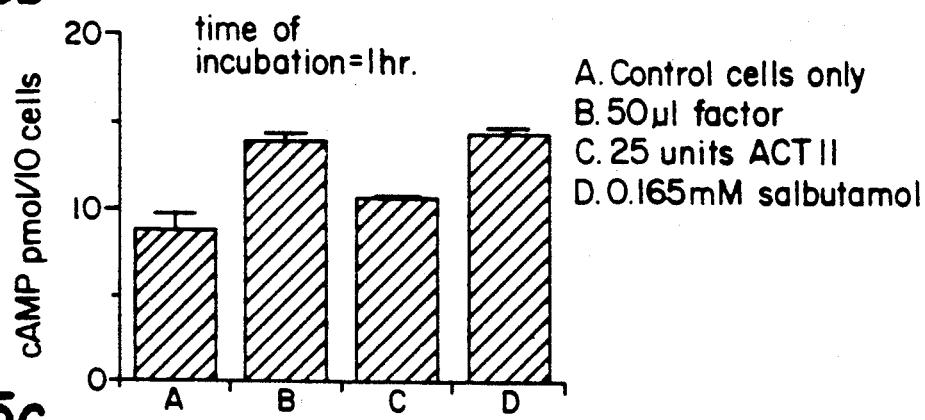
Figure 25C:
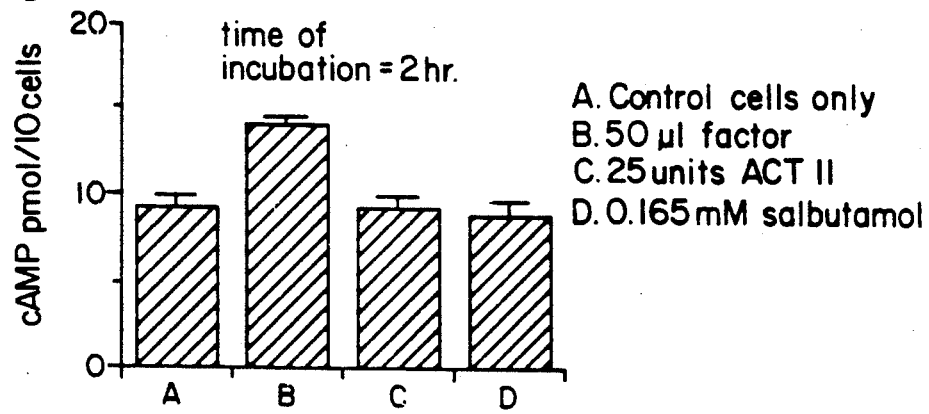

(control values for lipolytic activity for normal subjects range from 0.07 to 0.240 μmoles glycerol/ml urine or 0.5 to 1.88 μmoles glycerol/mg creatinine).

weight loss or cachexia this lipolytic factor is being over-produced and will generally be an agent that is responsible for the cachexia condition. In this connection, as previously mentioned, at least a rough qualitative relationship between extent of weight loss and lipolytic activity in body fluid samples tested has been already observed in a number of cases; also considered significant is the fact that it has been found that the lipolytic factor is effective in raising the level of cyclic adenylic acid (cAMP) at least in mouse adipose tissue cell preparations (adipocytes) and, unlike most hormones, this elevated cAMP level is maintained for a considerable time. This latter effect is illustrated in FIG. 25 wherein bar chart diagrams (a), (b) and (c) show the relative levels of cAMP measured in adipocytes from mouse adipose tissue after incubation for various periods with preparations of the lipolytic factor of this invention and, for comparison, with ACTH (the lipase activating adrenocorticotropic hormone) and with Salbutamol which are both known as other biologically active lipolytic agents.

Figure 26:
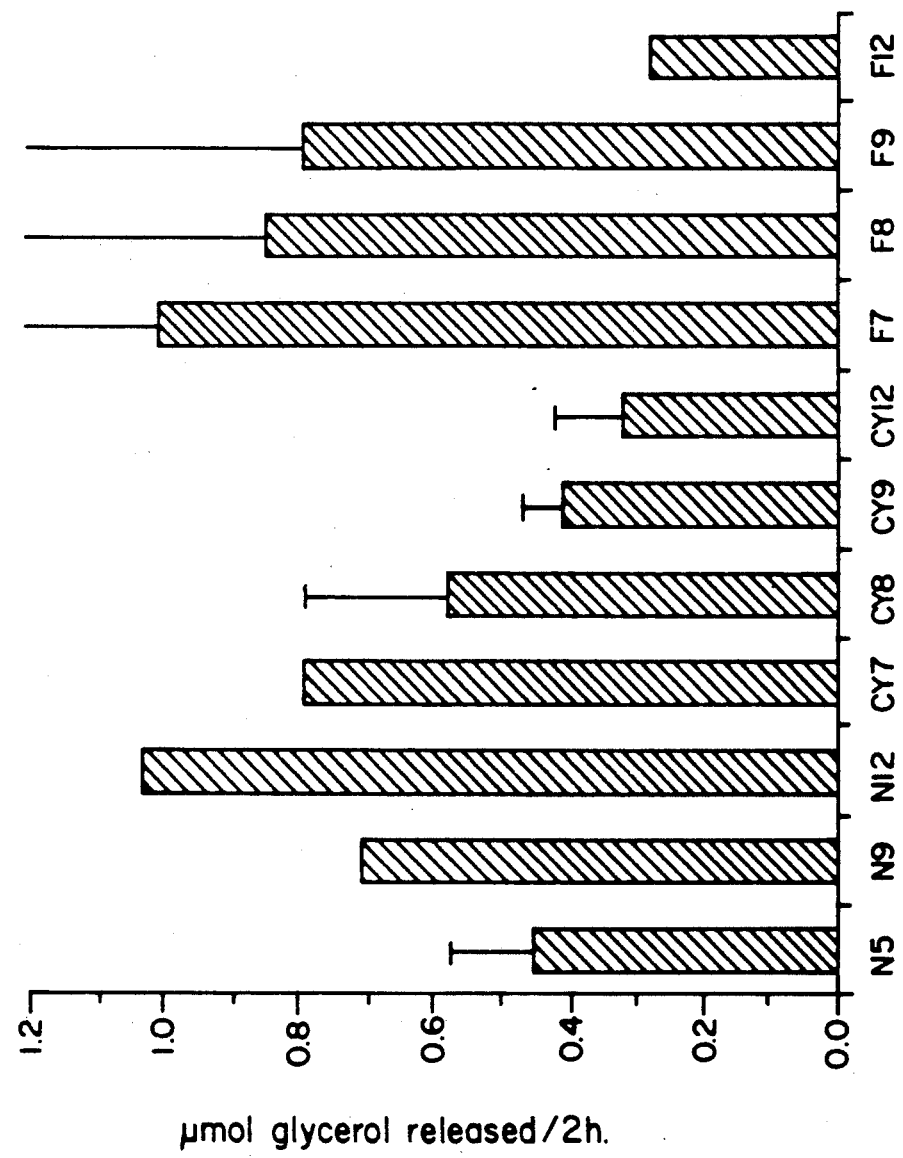
FIG. 26 is a bar chart diagram showing how assaying the lipolytic activity of urine samples can reflect tumour growth and the effect thereon of administering antitumour drugs (MAC13—Treated with cyclophosphamide & 5FU)

Another significant feature is the fact that there also usually appears to be a correlation between the amount of lipolytic activity in the body fluid samples and extent or rate of tumour growth, so that measurements of the activity of this lipolytic factor can provide useful information in monitoring the development of a cancer and progress thereof under treatment. Thus, it has been demonstrated for example that when MAC13 tumour bearing mice are treated with antitumour drugs such as cyclophosphamide or fluorouracil, after a few days an otherwise increasing level of lipolytic activity in the urine suddenly begins to decrease as the drugs begin to take effect. By way of example, this is illustrated in the bar chart diagram of FIG. 26 which represents the results of an experiment in which urinary lipolytic activity was measured in male NMRI mice, transplanted with the non cachectic MAC13 tumour, during tumour growth (N5, N9, N12 show the lipolytic activity for non-treated mice on days 5, 9 and 12) and after treatment with cyclophosphamide (200mg $kg^{-1}$ administered on days 7 and 8; see CY7, CY8, CY9 and CY12) or with 5-fluorouracil (100 mg $kg^{-1}$ administered on days 7 and 8; see F7, F8, F9, F12). Urine was collected during treatment by placing the animals in metabolic cages and urinary lipolytic activity was measured.

To show that the active lipolytic substance herein identified is not a product also associated with other conditions that cause weight loss in at least human subjects, similar tests were carried out, using the Sephadex G50 column techique, firstly on samples of urine collected and combined from a group of healthy human control subjects after 24 hours starvation, and secondly on samples of serum from weight loss patients suffering from Altzheimers disease. Although some of these samples did show lipolytic activity, in none of these other tests could any trace be found of the same main peaks of activity or characteristic distribution pattern of activity peaks in the fractions obtained from the Sephadex G50 columns, and there was therefore no evidence of the presence of the particular lipolytic factor of this invention. Similarly, with severe burns patients for whom serum samples show a very high level of lipolytic activity, no trace could be found of this particular lipolytic factor using the chromatographic techniques herein described.

Diagnostic Applications

For diagnostic purposes, to detect the presence of a tumour in a human patient or to monitor the progress thereof under treatment, basically it is simply necessary to take a sample of body fluid, such as blood plasma or serum, or preferably urine, which is then tested for the presence of the lipolytic factor herein identified, using for example a Sephadex G50 column or similar exclusion chromatography fractionating column and assaying the fractions obtained as described in order to determine the location and pattern of the main activity peaks, the results if necessary being compared to a reference or calibration standard which may be set up for providing some quantitative measure. The active lipolytic factor is thus treated as being a tumour marker substance.

In practice, any convenient method may be used for detecting and/or measuring this active lipolytic factor in the samples, and the apparatus and materials required may advantageously be packaged and supplied, together with appropriate practical instructions, in the form of self-contained diagnostic kits ready for immediate use. Particularly preferred diagnostic agents for detecting and/or measuring the active lipolytic factor in a convenient and reliable manner are biochemical reagents, such as monoclonal antibodies for example, capable of specifically recognizing and binding to the factor and then being identifiable by, for example, a visual change or a special screening assay using an associated labelled marker molecule, or by any other suitable technique known in the art.

The production of monoclonal antibodies to the lipolytic factor of this invention, or to individual active molecular species thereof, has previously been referred to and can be achieved by the use of established conventional techniques commonly used in the art. Such monoclonal antibodies, once prepared, may be immobilized on suitable solid supports (in a column for example) and then used for affinity purification to prepare in a convenient manner any further quantities that may be required of the purified active lipolytic factor from tumour extracts or body fluids.

It is envisaged, however, that a more important use of such monoclonal antibodies, apart from their use as a diagnostic agent, will be based on their properties as inhibitors or antagonists to the active lipolytic factor in human cancer patients and a consequent therapeutic value as agents for treating and suppressing the symptoms of cachexia and/or for preventing or reducing tumour growth. Thus, by virtue of this property, they can provide therapeutic agents and, more specifically, be used to make or manufacture a medical preparation or medicament for the therapeutic treatment of cancer-associated cachexia and/or malignant tumours in mammals.

Screening Applications

The finding of the widespread presence of this particular active lipolytic factor or material in association with malignant tumours at least in human cancer patients has supported the hypothesis that it is probably a product whose activity is likely to be beneficial for tumour development and growth, and that the presence of any agent which is antagonistic to, or an inhibitor of, the activity of this lipolytic factor could have at least potential human therapeutic value. Hence, preparations of the purified, or at least partially purified, lipolytic factor herein identified can be particularly useful, in accordance with a further aspect of the invention, for use in providing a convenient in vitro method of screening substances to find potential anti-cachectic and/or antitumour agents for therapeutic use. An example of this application is explained more fully below.

EXAMPLE 6

A series of in vitro experiments was conducted to screen a range of various compounds for possible activity as inhibitors or antagonists to the lipolytic factor. In general, in these experiments the compounds to be tested were added to extracts from MAC16 tumours and incubated with freshly prepared adipocytes from mouse epididymal adipose tissue for 2 hours. The lipolytic activity, or reduction thereof, was then determined by measuring the glycerol release using the enzyme assay method already described that results in a production of NAD from the reduced form NADH, the amount of NAD (corresponding to the amount of glycerol present) being measured spectro-photometrically as a decrease in absorption at 340nm.

More specific details of the experimental procedures in these inhibition studies are summarised below:

1. Preparation of extracts from MAC16 tumours

MAC16 tumours from NMRI mice that had lost up to one third of their original body weight, were homogenised in Krebs-Ringer buffer at a concentration of 0.2g/ml. The homogenate was then centrifuged and the supernatant used for inhibition studies.

2. Preparation of adipocytes

Fat pads were removed from 2 mice for the assay of each batch of 10 samples. 1 ml of collagenase solution in Krebs buffer (2mg/ml) was added to the fat pads from 1 mouse which were then finely chopped prior to incubation for 2 hour at 37° C. After 2 hours the adipocytes were pooled, washed three times in Krebs buffer, and then counted to obtain a concentration of $1.5-2.0 \times 10^5$ adipocytes per ml.

3. The experiments were set up as follows:

100μl tumour extract + 1 ml fat cells
Compound to be screened + 1 ml fat cells
100μl tumour and compound + 1 ml fat cells Each compound was tested at increasing concentrations and all samples were prepared and processed in duplicate.

The samples were gassed for 2 min with 95% $O_2$, 5% $CO_2$ mixture, mixed and incubated for 2 hour at 37° C. After 2 hour, 0.5 ml from each sample was then assayed for glycerol content.

Figure 23:
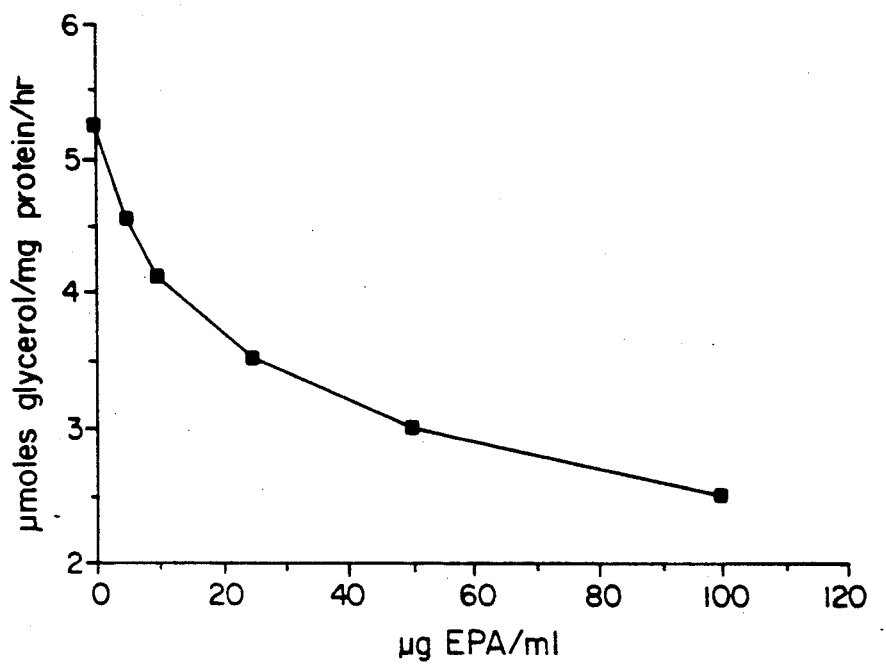
FIG. 23 is a diagram showing the effect of an inhibitor (EPA) on lipolytic activity of a MAC16 tumour extract (Effect of EPA on lipolytic activity)

Although these tests on many compounds failed to indicate any significant inhibition of the lipolytic factor in the tumour extracts, some compounds were found which did appear to show some significant degree of inhibition. These included hypoxanthine, Salbutamol, tolbutamide and, most notably, 5,8,11,14,17-eicosapentaenoic acid or a triglyceride ester thereof (herein referred to shortly as EPA) which is a component of marine oil. This particular compound, which is the subject of a copending U.K. patent application filed by us, was found to have a strong inhibitory effect on the lipolytic activity of the lipolytic factor in the tumour extracts, as illustrated for example by FIG. 23 of the accompanying drawings which is a diagram showing the results obtained using EPA in one set of the above experiments. This diagram also clearly indicates a dose dependence nature of the effect.

In general, the inhibitory effect observed in the in vitro experiments can be expected to occur also in vivo, and it is anticipated that by using this screening method further such antagonists or inhibitors will be found that will have useful therapeutic applications for the treatment of cancer-associated cachexia and/or as antitumour agents.

Thus, a further aspect the invention expressed in general terms consists in the use of an antilipolytic agent for the manufacture of a medical preparation or medicament for the treatment of cancer-associated cachexia and/or tumours, wherein said antilipolytic agent is a compound capable of specific activity as an antagonist to or inhibitor of the naturally produced tumour-associated lipolytic factor characterised as hereinbefore set forth.

In carrying out this aspect of the invention, in general a non-toxic and effective anti-cachexia or antitumour amount of the antagonist or inhibitor will be made up as a pharmaceutical formulation for administration in any suitable manner, for example orally, parenterally (including subcutaneously, intramuscularly and intravenously), or topically. Again, such formulations may be presented in unit dosage form and may comprise a pharmaceutical composition, prepared by any of the methods well known in the art of pharmacy, in which the active antagonist or inhibitor component is in intimate association or admixture with at least one other ingredient providing a compatible pharmaceutically acceptable carrier, diluent or excipient.

Such formulations suitable for oral administration may be presented as discrete units such as capsules, cachets, tablets or lozenges, each containing a predetermined non-toxic therapeutic amount of the active antagonist or inhibitor substance or compound, whilst for parenteral administration the formulations may comprise sterile liquid preparations of a similar predetermined amount of the active substance or compound contained in ampoules ready for use.

MAC16 Cell Line and Purification

Although it is quite feasible for preparations of the purified or partially purified active lipolytic factor in useful amounts to be produced as herein described from extracts of tumours, such as the MAC16 adenocarcinoma, grown in vivo, the more convenient and preferred source will usually be extracts of tumour tissue cell cultures, especially cultures of the MAC16 cell line previously referred to.

Figure 24:
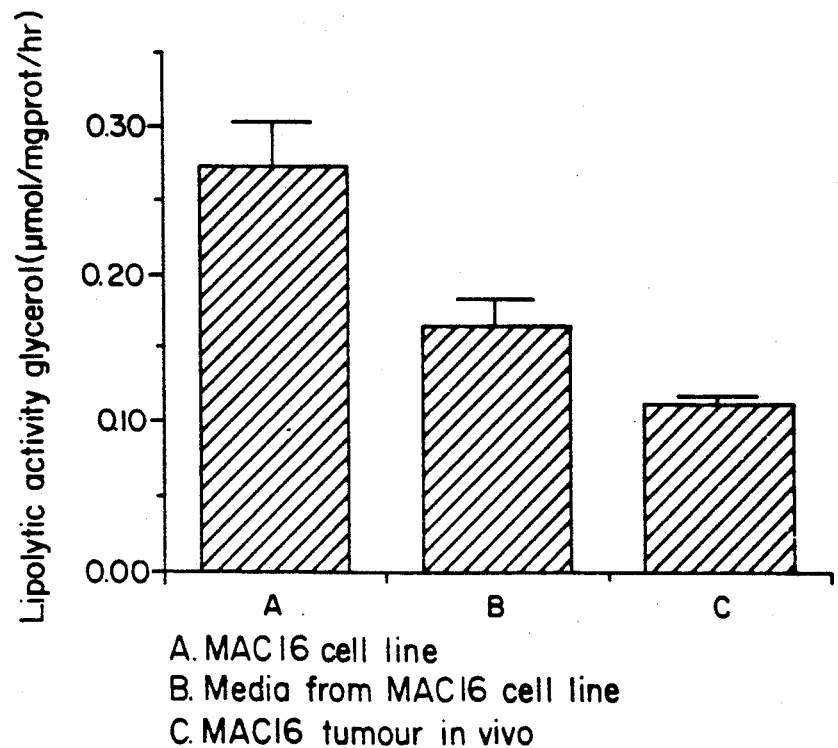
FIG. 24 is a bar chart diagram demonstrating the relative lipolytic activity of preparations from a MAC16 cell line culture (lipolytic activity of the MAC16 cell line)

The cells of this cell line are conveniently grown in RPMI 1640 media containing 10% foetal calf serum under an atmosphere of 10% $CO_2$ in air. When assayed in the adipocyte glyerol release assay method the cells have been found to release a greater amount of glycerol than do corresponding amounts of the tumour in vivo. Media collected from cells which had reached confluence also released more glycerol than the tumour in vivo. This is illustrated in FIG. 24.

Results for the cachectic activity of this cell line in vivo are illustrated in Table 4.

TABLE 4

| | Cell line cachectic activity in vivo | | |
|---|---|---|---|
| | weight loss (g) | food intake (g) | water intake (ml) |
| control | 0.00 ± 0.00 | 4.50 ± 0.50 | 4.00 ± 0.20 |

TABLE 4-continued

| MAC16 cells | 4.82 ± 1.14 | 3.60 ± 1.70 | 3.70 ± 0.20 |

$2.6 \times 10^6$ MAC16 cells were transplanted into female NMRI mice.
Weight loss was recorded 14 days after transplantation.
The results are expressed as the Mean ± S.E.M. The number of animals studied was 6 to 10.

In purifying or at least partially purifying the cachectic lipolytic factor from extracts of such cell cultures, after stages of gel filtration chromatography as described, e.g. Sephadex G150 followed by Biogel P4 (Biogel P4 may be more effective in removing excess salt than Sephadex G50), pooled and freeze-dried active fractions may then be subjected to hydrophobic chromatography using for example a C18 column. The fractions so obtained may be subsequently again pooled and freeze-dried or lyophilized for further purification, if required, by high performance liquid chromatography (HPLC) using, for example, Biogel P2, DEAE cellulose and Biogel P2 columns in succession.

Molecular Composition

As has been shown by the results of the gel filtration exclusion chromatographic separations, the active lipolytic factor of this invention generally appears to comprise active components having molecular weights of about 700 to 800 daltons, 1500 daltons and 3000 daltons or slightly greater, but the ratio of activity between these components is rather variable and in some cases not all three peaks of activity are evident in the chromatograms. However, the approximate ratio of 1:2:4 between these molecular weight values is deemed significant and it is believed that a basic active lipolytic substance is the species having a molecular weight in the range of about 700 to 800 daltons, say approximately 750 daltons, and that the other higher molecular weight species are the result of aggregation between molecules of the smaller species, possibly promoted by or involving metal ions. Additionally, there are also some indications, (especially from isoelectric focussing experiments) suggesting that even the molecular species of 700 to 800 daltons may, at least in some conditions of acidity and ionic strength, be resolved into an even smaller active species of about half this molecular weight.

Figure 29:
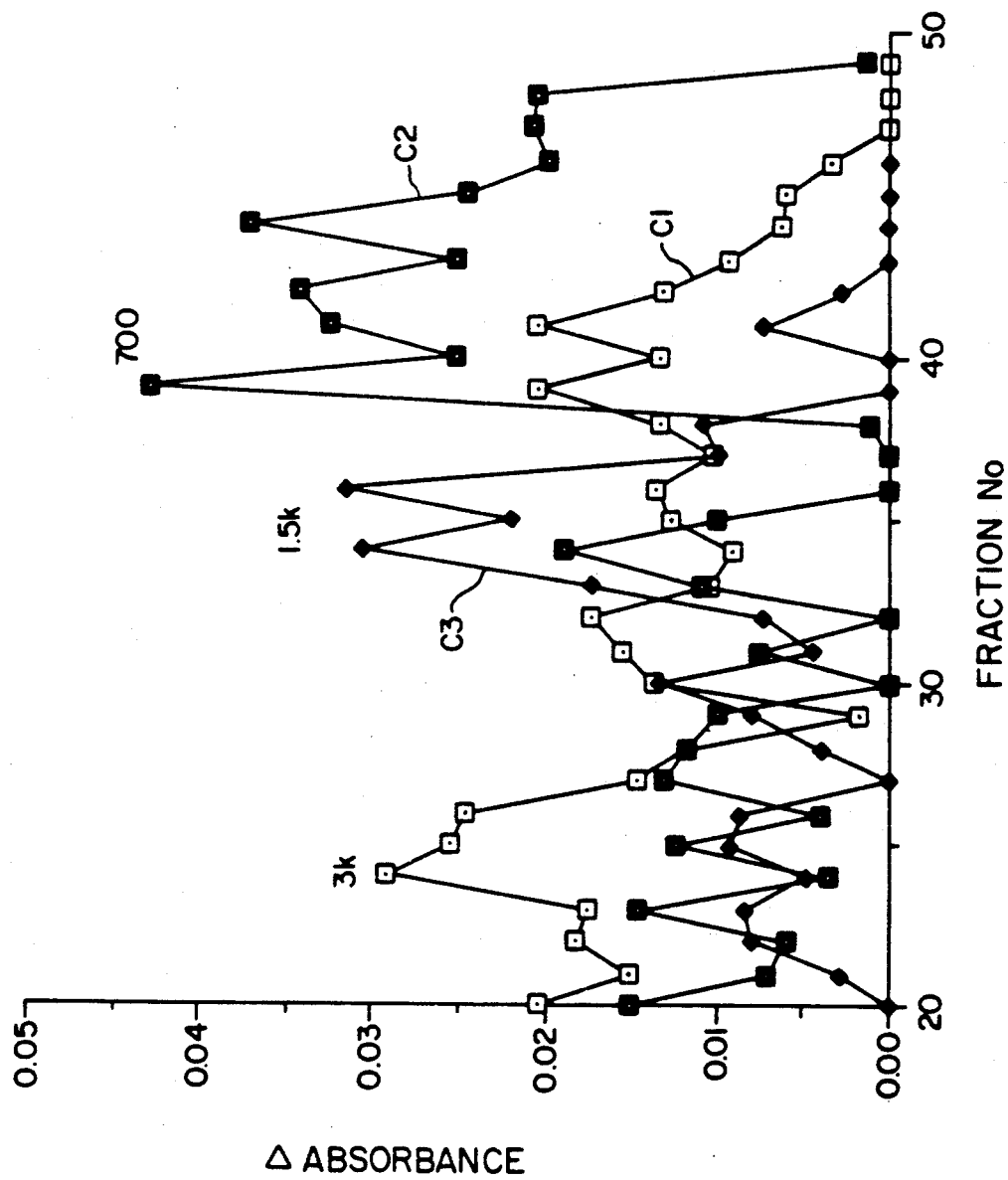
FIG. 29 is a diagram showing the effect on the lipolytic activity distribution pattern obtained after adding EDTA and also the effect obtained after subsequently adding calcium ions (Effect of EDTA and calcium on elution of lipolytic factor from sephadex G50).

Some significant evidence for the aggregation of a lower molecular weight species and the involvement of metal ions, in particular, is provided by the results of an experiment, illustrated in FIG. 29, in which a sample of the lipolytic material was treated with ethylenediaminetetra-acetic acid (EDTA) and then subjected to gel filtration using a Sephadex G50 column. Whilst a control sample of the lipolytic material gave the usual characteristic pattern of three main activity peaks at about 3,000 daltons, 1,500 daltons and 700 daltons (see curve C1), it will be seen (curve C2) that after the EDTA treatment the 3,000 daltons peak at least was greatly diminished but there was a considerable increase in the lower molecular weight peak or peaks at about and/or below 700–800 daltons. In that EDTA is well known to be a strong chelating agent, it seems reasonable to suppose that in this case it acts to remove metal ions binding together the smaller molecular species and much of the 3,000 daltons species then breaks up into the smaller components. On subsequently adding calcium ions to the EDTA sample and repeating the gel filtration it was then found that the activity of the 700 daltons species was reduced and the main activity peaks corresponded to the 1,500 daltons species (see curve C3), this being consistent with these added metal ions promoting an increase again in aggregation of the smaller species.

Figure 27:
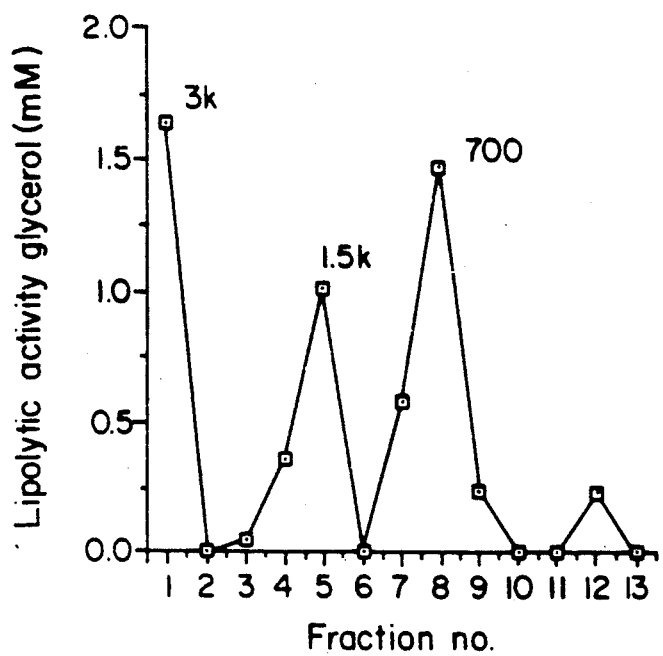
FIG. 27 is a diagram of a chromatogram showing the lipolytic activity distribution pattern of fractions obtained by HPLC hydrophobic chromatography in passaging a sample of the partially purified lipolytic material of the present invention through a C4 butyl column (H.P.L.C.: C4 hydrophobic chromatography of partially purified lipolytic factor)
Figure 28:
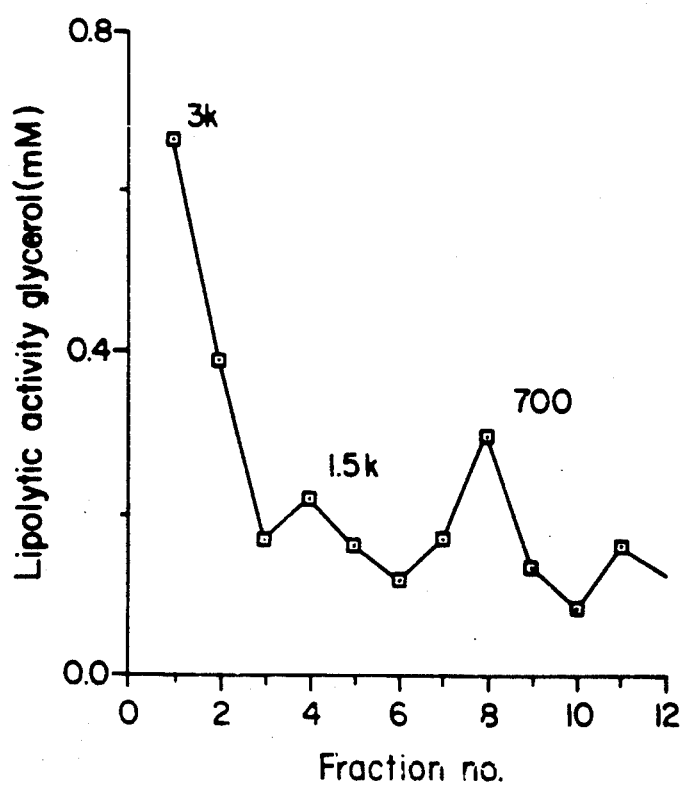
FIG. 28 is a diagram similar to FIG. 27 of a chromatogram showing the lipolytic activity distribution pattern of fractions obtained by re-passaging through a C4 butyl column of fractions that provided one only of the major activity peaks shown in FIG. 27 during the earlier first passage of a sample of the active material through the column (H.P.L.C.: C4 rechromatography of peak 1 obtained from purified factor)

Moreover, there is also some evidence indicating that there is generally some kind of equilibrium condition existing between these different species. Thus, if fractions collected from one single large activity peak after passage of a sample of a preparation of the lipolytic factor through a hydrophobic C4 butyl column in carrying out high performance liquid chromatography (HPLC) are re-passaged through the column, all three main peaks have been found to reappear. This is illustrated in FIGS. 27 and 28. FIG. 27 shows the result of the first passage of the initial sample of an at least partially purified preparation of the lipolytic factor, and FIG. 28 shows the result of rechromatographing fractions from the first major activity peak shown in FIG. 27. In each case, Sephadex G50 chromatography confirmed that the three main peaks in both FIGS. 27 and 28 corresponded (respectively in order of elution) to molecular weights of approximately 3000, 1500 and 700–800 daltons. Other similar evidence also supports this hypothesis of an equilibrium condition, and it is also consistent with the hypothesis of aggregation of the smaller molecular species dependent on the presence of metal ions.

In some cases, the active components may also pick up or bind other molecules giving apparently spurious peaks, this possibility being consistent with high adhesive properties of the material which have often become apparent in carrying out the various purification or attempted purification procedures.

REFERENCES (1) Bibby, M.C., Double, J.A., Ali, S.A., Fearon, K.C.H., Brennan, R.A. and Tisdale, M.J. 1987). *J. Natl. Cancer Inst.,* 78, 539–546.

(2) Beck, S.A. and Tisdale, M.J. (1987). *Cancer Research,* 47, 5919–5923.

(3) Kitada, S., Hays, E.F., and Mead J.F. (1980), *Lipids* 15 168–174.

(4) Kitada, S., Hays, E.F., and Mead J.F. (1981), *Prog. in Lipid Research,* 823–826.

(5) Kitada, S., Hays, E.F. and Mead, J.F. (1982). *J. Cell. Biochem.,* 20, 409–416.

(6) Masuno, H., Yoshimura, H., Ogawa, N. and Okuda, H. (1984). *Eur. J. Cancer Clin. Oncol.,* 20, 1177–1185.

(7) Masuno, H., Yamasaki, N., and Okuda, H. (1981), *Cancer Res.,* 41, 284–288.

8) Cowen, D.M., Double, J.A. and Cowen, P.N. (1980), *JNCI,* 64, 675–681.

(9) Wieland, O. (1974), in *"Methods of Enzymatic Analysis"* (Ed. Bergmeyer, H.U.) Vol. 3. pp1404–1409. Academic Press, N.Y.

(10) Cerami, A. et al (1985), Immunol. Lett., 11, 173

(11) Beutler, B. and Cerami, A. (1986), *Nature,* 320, 584.

(12) Mahony, S M., Beck, S.A. and Tisdale, M.J. (1988), *Br. J. Cancer,* 57, 385–389.

We claim:

1. A biologically active lipolytic polypeptide material produced from an extract or sample of biological source material by an isolation and purification production procedure that includes at least one stage of gel filtration exclusion chromatography in which at least a part of said extract or sample is applied to a column containing a filtration gel having a porosity adapted to retain material of molecular weight in the range of 600–4000 daltons, followed by recovering the retained material and selecting an active fraction or fractions thereof, said biological source material being selected from the group consisting of:
- a mammalian tumor tissue of a cachexia inducing tumor,
- a culture of mammalian tissue cells of a cachexia inducing tumor, and
- a body fluid of a mammal bearing a cachexia inducing tumor, said lipolytic polypeptide material having the following characteristics (a) it produces weight loss cachectic symptoms when administered by injection to healthy non-tumor bearing mice, (b) it is resolvable into at least one main active lipolytic component comprising a molecular species having a molecular weight of about 1500 daltons as determined by gel filtration exclusion chromatography, (c) it is resistant to trypsin, chymotrypsin, periodate, RNAase and DNAase, insofar as its lipolytic activity is concerned when solutions thereof are tested by in vitro assaying of glycerol released upon incubation with mouse adipose tissue, but said lipolytic activity is at least partially destroyed or inhibited by both pronase and alkaline phosphatase, (d) when tested as specified in (c) above, its lipolytic activity is inhibited by compounds selected from the group consisting of hypoxanthine, Salbutamol, tolbutamide, 5,8,11,14,17-eicosapentaenoic acid and a triglyceride of 5,8,11,14,17-eicosapentaenoic acid, (e) when incubated in vitro with adipocytes prepared from mouse adipose tissue, it promotes the establishment of an elevated level of cyclic adenylic acid (cAMP) in such cells.

2. A biologically active lipolytic material as claimed in claim 1 wherein said isolation and purification production procedure includes a preliminary stage of cation exchange column chromatography in which said extract or sample of the biological source material is applied first to a DEAE cellulose or other cationic stationary phase and the adsorbed material is eluted under a salt gradient to provide one or more active fractions for input to said at least one stage of gel filtration exclusion chromatography.

3. A material as claimed in claim 1 which also comprises an active lipolytic component represented by a molecular species having a molecular weight within the range of about 700–800 daltons as determined by gel filtration exclusion chromatography.

4. A material as claimed in claim 1 which also comprises an active lipolytic component represented by a molecular species having a molecular weight of about 3000 daltons as determined by gel filtration exclusion chromatography.

5. A material as claimed in claim 1 having a further characteristic that it is resolvable by gel filtration exclusion chromatography using a calibrated Sephadex G50 column or equivalent to provide a lipolytic activity distribution pattern of eluted fractions having main lipolytic activity peaks corresponding to a molecular species having a molecular weight of about 1500 daltons and to molecular species of which the a molecular weight is in the range of about 700–800 daltons or of which the a molecular weight is about 3000 daltons, or of which the a molecular weight has at least two values in the range of about 700–800 daltons and of about 3000 daltons respectively.

6. A material as claimed in claim 1 having a further characteristic that it is isolated from an extract of a culture of a MAC16 tumor cell line having a deposit accession number 89030816 in the European Collection of Animal Cell Cultures (ECACC).

7. A material as claimed in claim 1 having a further characteristic that it is isolated from a sample of urine or blood serum of a mammal bearing a cachexia-inducing tumor.

8. A biologically active lipolytic polypeptide material isolated from an extract of a culture of a MAC16 tumor cell line having a deposit accession number 89030816 in the European Collection of Animal Cell Cultures (ECACC), said polypeptide material being resolvable by gel filtration exclusion chromatography using a calibrated Sephadex G50 column or equivalent to provide a lipolytic activity distribution pattern of eluted fractions having main lipolytic activity peaks corresponding to a molecular species having a molecular weight of about 1500 daltons and to molecular species of which the a molecular weight is in the range of about 700–800 daltons or of which the a molecular weight is about 3000 daltons, or of which the a molecular weight has at least two values in the range of about 700–800 daltons and of about 3000 daltons respectively.

9. A purified or partially purified biologically active lipolytic polypeptide material having the following characteristics:

(1) it has an average molecular weight;

(2) it is obtainable from mammalian cachexia-inducing tumors, cultures of mammalian tissue cells of cachexia-inducing tumors, or body fluids such as urine or blood serum of mammals bearing cachexia-inducing tumors, by subjecting extracts of said tumors or of said tissue cell cultures or samples of said body fluids to an isolation and purification procedure that includes at least one stage of gel filtration exclusion chromatography wherein at least a part of said extract or sample is applied to a column containing a filtration gel having a porosity adapted to retain material of molecular weight in the range of 600–4000 daltons, followed by recovering the retained material and selecting an active fraction or fractions thereof;

and having the further characteristics:

(a) it comprises a plurality of active molecular species of different molecular weights with the higher molecular weight species being susceptible to breakdown into the lower molecular weight species;

(b) it is resolvable by gel filtration exclusion chromatography using a calibrated Sephadex G50 column or equivalent to provide a lipolytic activity distribution pattern of eluted fractions having main lipolytic activity peaks corresponding to a molecular species having a molecular weight of about 1500 daltons and to molecular species of which the a molecular weight is in the range of about 700–800 daltons or of which the a molecular weight is about 3000 daltons, or of which the a molecular weight has at least two values in the range of about 700–800 daltons and of about 3000 daltons respectively.

(c) it is resistant to trypsin, chymotrypsin, periodate, RNAase and DNAase, insofar as its lipolytic activity is concerned when solutions thereof are tested by in vitro assaying of glycerol released upon incubation with mouse adipose tissue, but said lipolytic activity is at least partially destroyed or inhibited by both pronase and alkaline phosphatase;

(d) when tested as specified in (c) above, its lipolytic activity is inhibited by compounds selected from the group consisting of hypoxanthine, Salbutamol, tolbutamide, 5,8,11,14,17-eicosapentaenoic acid and a triglyceride of 5,8,11,14,17-eicosapentaenoic acid;

(e) when incubated in vitro with adipocytes prepared from mouse adipose tissue, it promotes the establishment of an elevated level of cyclic adenylic acid (cAMP) in such cells;

(f) it produces weight loss cachectic symptoms when fresh preparations thereof are administered by injection to healthy non-tumor bearing mice;

(g) it is obtainable as specified in (2) above wherein said isolation and purification production procedure includes a preliminary stage of cation exchange column chromatography in which said extract or sample of the biological source material is applied first to a DEAE cellulose or other cationic stationary phase and the adsorbed material is eluted under a salt gradient to provide one or more active fractions for input to said at least one stage of gel filtration exclusion chromatography.

* * * * *